US008468890B2

(12) United States Patent
Shimazaki et al.

(10) Patent No.: US 8,468,890 B2
(45) Date of Patent: Jun. 25, 2013

(54) ULTRASONIC DETECTION DEVICE, ULTRASONIC DETECTION METHOD, AND ATOMIC POWER PLANT NONDESTRUCTIVE INSPECTION METHOD

(75) Inventors: Masanori Shimazaki, Hyogo (JP); Masayuki Takeishi, Hyogo (JP); Tomoyuki Hirayama, Hyogo (JP); Yoshinori Shimada, Osaka (JP); Oleg Kotiaev, Osaka (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 497 days.

(21) Appl. No.: 12/670,788

(22) PCT Filed: Aug. 8, 2008

(86) PCT No.: PCT/JP2008/064326
§ 371 (c)(1),
(2), (4) Date: Jan. 26, 2010

(87) PCT Pub. No.: WO2009/022658
PCT Pub. Date: Feb. 19, 2009

(65) Prior Publication Data
US 2010/0206082 A1 Aug. 19, 2010

(30) Foreign Application Priority Data

Aug. 10, 2007 (JP) .................. 2007-209550
Apr. 28, 2008 (JP) .................. 2008-117429

(51) Int. Cl.
*G01N 29/00* (2006.01)
(52) U.S. Cl.
USPC ............................... 73/628; 73/627
(58) Field of Classification Search
USPC .................................... 73/627, 628
See application file for complete search history.

(56) References Cited

U.S. PATENT DOCUMENTS

| 4,137,991 | A | * | 2/1979 | Melcher et al. ............... 181/142 |
| 5,457,997 | A | | 10/1995 | Naruo et al. |
| 6,181,431 | B1 | * | 1/2001 | Siu ............................... 356/502 |
| 6,328,697 | B1 | | 12/2001 | Fraser |
| 6,443,901 | B1 | | 9/2002 | Fraser |
| 6,490,047 | B2 | | 12/2002 | Siu |
| 6,632,178 | B1 | * | 10/2003 | Fraser ........................... 600/459 |
| 7,421,900 | B2 | | 9/2008 | Karasawa et al. |
| 7,463,363 | B2 | | 12/2008 | Drake, Jr. et al. |
| 2001/0039836 | A1 | * | 11/2001 | Ogawa .......................... 73/608 |
| 2010/0206082 | A1 | | 8/2010 | Shimazaki et al. |

FOREIGN PATENT DOCUMENTS

| EP | 1152240 A2 | 11/2001 |
| JP | 58-11639 B2 | 3/1983 |

(Continued)

OTHER PUBLICATIONS

United States Office Action dated Feb. 23, 2012, issued in related U.S. Appl. No. 12/517,234.

(Continued)

*Primary Examiner* — Hezron E Williams
*Assistant Examiner* — Gregory J Redmann
(74) *Attorney, Agent, or Firm* — Westerman, Hattori, Daniels & Adrian, LLP

(57) ABSTRACT

Provided are an ultrasonic inspection device, an ultrasonic inspection method, and an atomic power plant nondestructive inspection method that are capable of efficiently generating ultrasonic waves having a sufficient intensity and that are capable of carrying out preferable inspection in a wide range. Provided is an ultrasonic inspection device including a laser device that emits output-adjusted laser light and a volumetric inspection ultrasonic-wave transmitting unit having a transmitting diaphragm that generates ultrasonic waves upon being irradiated with the laser light emitted by the laser device, inspection being carried out by radiating the ultrasonic waves generated by the transmitting diaphragm of the volumetric inspection ultrasonic-wave transmitting unit on a structural member, wherein the transmitting diaphragm is formed of titanium.

25 Claims, 16 Drawing Sheets

FOREIGN PATENT DOCUMENTS

| | | |
|---|---|---|
| JP | 7-306188 A | 11/1995 |
| JP | 10-288607 A | 10/1998 |
| JP | 11-326580 A | 11/1999 |
| JP | 2984390 B2 | 11/1999 |
| JP | 2000-028589 A | 1/2000 |
| JP | 2002-17723 A | 1/2002 |
| JP | 2002-328116 A | 11/2002 |
| JP | 2004-503312 A | 2/2004 |
| JP | 2004-321574 A | 11/2004 |
| JP | 2005-043139 A | 2/2005 |
| JP | 2005-175919 A | 6/2005 |
| JP | 2005-253751 A | 9/2005 |
| SU | 1804837 A1 | 3/1993 |

OTHER PUBLICATIONS

Foreign Associate letter dated Sep. 20, 2010, summarizing Russian Office Action dated Aug. 20, 2010. cited in corresponding U.S. Appl. No. 12/517,234.

Chinese Office Action dated Mar. 30, 2011, issued in corresponding Chinese Patent Application No. 200880001377.1. cited in corresponding U.S. Appl. No. 12/517,234.

E. Biagi et al., "Fully Fiber Optic Ultrasonic Probes For Virtual Biopsy"; 2006 IEEE Ultrasonic Symposium, pp. 556-559. cited in corresponding U.S. Appl. No. 12/517,234.

International Search Report of PCT/JP2008/050973, Mailing Date of Apr. 15, 2008. cited in corresponding U.S. Appl. No. 12/517,234.

International Search Report of PCT/JP2008/064326, mailing date of Nov. 11, 2008.

Chinese Office Action dated Sep. 19, 2012, issued in corresponding Chinese Patent Application No. 200880102430.7, with English translation (24 pages).

Zhang et al., "Review of Diamond Film and High-Fidility Acoustic Diaphragm Materials", Chinese Journal of Materials Research, Aug. 1994; vol. 8, No. 4; pp. 330-336.

Decision on Patent Grant dated Feb. 17, 2011, issued in corresponding Russian Patent Application No. 2010102123.

Russian Office Action dated Oct. 27, 2010, issued in corresponding Russian Patent Application No. 2010102123/28(002973).

Japanese Decision to Grant a Patent dated Apr. 2, 2013, issued in cooresponding Japanese Patent Application No. 2008-117429, w/ English translation.

\* cited by examiner

— □ 2mm;83.4mJ
—·—·— △ 4mm;88mJ

— □ 2mm;157mJ
—·—·— △ 4mm;164mJ

ULTRASONIC DETECTION DEVICE, ULTRASONIC DETECTION METHOD, AND ATOMIC POWER PLANT NONDESTRUCTIVE INSPECTION METHOD

TECHNICAL FIELD

The present invention relates to an ultrasonic detection device, an ultrasonic detection method, and an atomic power plant nondestructive inspection method.

BACKGROUND ART

Detection devices employing ultrasonic waves have been applied in, for example, medicine, nondestructive internal inspection of atomic power plants, etc. For example, because ultrasonic testing can relatively easily detect internal flaws of materials, it has been playing an important role, employed in inspection of critical parts of structural materials. In ultrasonic testing, for example, as disclosed in Patent Document 1, a piezoelectric element has been employed to transmit ultrasonic waves.

Because this piezoelectric element is relatively large, for example, having a diameter of about 20 mm, the device is also large. Accordingly, testing of narrow spaces or members having complicated shapes is difficult. In addition, because the frequency band of the ultrasonic waves is constrained by the intrinsic frequency of the piezoelectric element, it is not ideal for applications such as displaying an image of a member surface, etc.

As a way of alleviating these, for example, a laser ultrasonic method disclosed in Patent Document 2 has been proposed.

Here, laser light is radiated on a test object using an optical fiber, ultrasonic waves are generated at the surface of the test object by this laser light, and the ultrasonic waves transmitted through the test object are detected using receiving laser light. A flaw is detected by recognizing variations in these ultrasonic waves, and depth can also be determined by performing a frequency analysis of the received ultrasonic waves.

In other words, because a thin optical fiber is used in generating the ultrasonic waves, the size of the device can be reduced, and it is possible to cope with testing of narrow spaces or members having complicated shapes.

In addition, for example, it has been proposed to generate ultrasonic waves using laser light, as disclosed in Patent Document 3, and to carry out nondestructive inspection using these ultrasonic waves.

Here, laser light is radiated into a tubular object, which is closed at one end with a metal plate and whose interior is filled with gas, thereby inducing a change due to thermal expansion of the internal gas and the thermal stress of the metal plate, and the ultrasonic waves are generated by propagating this change to the outside.

Patent Document 1: Japanese Unexamined Patent Application, Publication No. 2000-28589.
Patent Document 2: Japanese Unexamined Patent Application, Publication No. 2005-43139
Patent Document 3: the Publication of Japanese Patent No. 2984390.

DISCLOSURE OF INVENTION

With the method disclosed in Patent Document 2, because the laser light is directly radiated on the test object, the test object may be degraded or deformed.

Additionally, this restricts the intensity of the laser light, thus preventing an adequate investigation, or limiting the range of test objects to be inspected.

Furthermore, it is not possible to carry out inspection in places where the laser light cannot pass through, for example, in sodium, which is used as coolant for a fast-breeder reactor.

With the method disclosed in Patent Document 3, the degradation or the deformation of the test object is resolved because the laser light is not directly radiated on the test object. Incidentally, the ultrasonic wave intensity needs to be sufficiently increased in order to carry out nondestructive inspection using ultrasonic waves; however, because this point is not specifically described in Patent Document 3, implementation thereof without modifications is not possible.

In addition, there is a strong demand for an ultrasonic inspection device having a specific aspect that is capable of generating ultrasonic waves of optimal intensity or directivity in accordance with the types of test object or inspection types, thus being capable of coping with a diverse range of inspections.

The present invention has been conceived in light of the above-described situations, and an object thereof is to provide an ultrasonic inspection device, an ultrasonic inspection method, and a nondestructive atomic power plant inspection method that are capable of efficiently generating sufficiently intense ultrasonic waves, as well as carrying out desired inspection in a wide range.

Further, another object thereof is to provide an ultrasonic inspection device, an ultrasonic inspection method, and a nondestructive atomic power plant inspection method that are capable of generating ultrasonic waves of optimal intensity or directivity in accordance with the types of test object or inspection types, thus being capable of coping with a diverse range of inspections.

In order to solve above-described problems, the present invention employs the following solutions.

A first aspect of the present invention is an ultrasonic inspection device including a laser device that emits output-adjusted laser light and an ultrasonic-wave transmitting unit having a transmitting diaphragm that generates ultrasonic waves upon being irradiated with the laser light emitted by the laser device, inspection being carried out by irradiating a test object with the ultrasonic waves generated by the transmitting diaphragm of the ultrasonic-wave transmitting unit, wherein the transmitting diaphragm is formed of titanium.

In addition, a second aspect of the present invention is an ultrasonic inspection device including a laser device that emits output-adjusted laser light and an ultrasonic-wave transmitting unit having a transmitting diaphragm that generates ultrasonic waves upon being irradiated with the laser light emitted by the laser device, inspection being carried out by irradiating a test object with the ultrasonic waves generated by the transmitting diaphragm of the ultrasonic-wave transmitting unit, wherein the transmitting diaphragm is formed of aluminum.

With the first aspect or the second aspect, the transmitting diaphragm is irradiated with the output-adjusted laser light emitted by the laser device, and thus the transmitting diaphragm generates the ultrasonic waves, and because these ultrasonic waves are radiated on a test object, it is possible to prevent degradation or deformation of the test object.

Accordingly, high-power laser light can be handled, and therefore, the intensity of the generated ultrasonic waves can be increased. Thus, preferable inspection can be carried out.

In addition, because adequate inspection can be carried out even if there is a large distance to the test object, the directivity can be increased. Because the resolution can be reduced thereby, the inspection precision can be improved.

The applicants, as a result of rigorous evaluation, have discovered that titanium and aluminum generate high-intensity ultrasonic waves and are useful as transmitting diaphragms. In addition, a transmitting diaphragm formed of titanium or aluminum is also useful in that, compared with other materials, high-intensity ultrasonic waves are generated therefrom, in response to the energy input to the transmitting diaphragm from the laser light. Because of the high energy efficiency as described above, it is possible to efficiently generate sufficiently intense ultrasonic waves.

Furthermore, a third aspect of the present invention is an ultrasonic inspection device including a laser device that emits output-adjusted laser light and an ultrasonic-wave transmitting unit having a transmitting diaphragm that generates ultrasonic waves upon being irradiated with the laser light emitted by the laser device, inspection being carried out by irradiating a test object with the ultrasonic waves generated by the transmitting diaphragm of the ultrasonic-wave transmitting unit, wherein the transmitting diaphragm is restrained on the laser incident side by an optical member.

The applicants, as a result of rigorous evaluation, have discovered that the intensity of the generated ultrasonic waves can be increased by restraining the transmitting diaphragm with an optical member. This can be considered to be due to, for example, the following phenomenon.

Because the laser incident side of the transmitting diaphragm is restrained by the optical member, when the laser light is radiated on the transmitting diaphragm causing deformation thereof, the deformation acts on the optical member. Then, because the reaction force from the optical member is exerted on the transmitting diaphragm in the direction of the ultrasonic wave generation, the intensity of the ultrasonic waves generated by the transmitting diaphragm is increased.

Additionally, because the optical member suppresses degradation of or damage to the transmitting diaphragm by the laser light, the intensity of the generated ultrasonic waves can be increased by increasing the intensity of the laser light.

Note that glass of sapphire, silica, etc., or ceramic etc. of oxidized aluminum film, etc. is employed as the optical member.

Furthermore, the optical member and the transmitting diaphragm may be bonded or may simply be disposed adjacent to each other.

In addition, a fourth aspect of the present invention is an ultrasonic inspection device including a laser device that emits output-adjusted laser light and an ultrasonic-wave transmitting unit having a transmitting diaphragm that generates ultrasonic waves upon being irradiated with the laser light emitted by the laser device, inspection being carried out by irradiating the test object with the ultrasonic waves generated by the transmitting diaphragm of the ultrasonic-wave transmitting unit, wherein jelly-like viscous material is applied on the laser incident side surface of the transmitting diaphragm.

The applicants, as a result of rigorous evaluation, have discovered that the intensity of the generated ultrasonic waves is increased by applying a jelly-like viscous material on the laser incident side surface of the transmitting diaphragm. This can be considered to be due to, for example, the following phenomenon.

Of vibrations generated at the transmitting diaphragm by radiating the laser light on the transmitting diaphragm, vibrations directed toward the laser incident side are reflected backwards by the jelly-like viscous material; therefore, these vibrations are directed in the direction opposing the laser incident side, that is, the direction of the ultrasonic wave generation. In this way, because the vibrations directed in the direction of the ultrasonic wave generation are superimposed on the vibrations directed in the opposite direction and reflected backward, the intensity of the ultrasonic waves generated by the transmitting diaphragm is increased.

In addition, because the jelly-like viscous material is easily deformed, it can be made to adhere to the surface of the transmitting diaphragm without a gap. Accordingly, because the viscous material can reflect back the vibrations of the transmitting diaphragm over the entire surface thereof, energy can be efficiently transmitted in the direction of the ultrasonic wave generation.

Note that it is preferable that the jelly-like viscous material be transparent. By doing so, because transparent viscous material does not prevent the passage of the laser light, more laser light is made incident on the transmitting diaphragm; therefore, the intensity of the generated ultrasonic waves can be increased.

Additionally, the region over which the jelly-like viscous material is applied need not be the entire surface so long as at least the region that is irradiated with the laser light is covered. It is more desirable that the viscous material be applied so as to cover portions where the ultrasonic wave generation is greater, beyond the region that is irradiated with the laser light.

Furthermore, a fifth aspect of the present invention is an ultrasonic inspection device including a laser device that emits output-adjusted laser light of adjusted power and an ultrasonic-wave transmitting unit having a transmitting diaphragm that generates ultrasonic waves upon being irradiated with the laser light emitted by the laser device, inspection being carried out by irradiating the test object with the ultrasonic waves generated by the transmitting diaphragm of the ultrasonic-wave transmitting unit, the ultrasonic inspection device including beam-diameter adjusting means for adjusting the beam diameter of the laser light radiated on the transmitting diaphragm.

In addition, the first to the fourth aspects described above may be configured to include the beam-diameter adjusting means for adjusting the size of the beam diameter of the laser light radiated on the transmitting diaphragm.

The applicants, as a result of rigorous evaluation, have discovered that the directivity of the laser light changes depending on the beam diameter thereof and that, even with the same amount of energy, the intensity of the ultrasonic waves generated by the transmitting diaphragm differs, that is, the mode of ultrasonic wave generation of the transmitting diaphragm differs.

In short, because the directivity is increased by decreasing the beam diameter, in other words, high-intensity ultrasonic waves can be output in a wide region, this is effective for, for example, surface inspection wherein a surface is inspected by imaging it. On the other hand, because the directivity is decreased by increasing the beam diameter, in other words, high-intensity ultrasonic waves are output concentrated in a limited region, this is effective for, for example, volumetric inspection for inspecting internal flaws.

In this way, by providing the beam-diameter adjusting means, it is possible to cope with changes in types of test object, inspection location, etc. with a single ultrasonic inspection device. In addition, it is possible to carry out inspection of differing characteristics, for example, volumetric inspection and surface inspection, i.e. hybrid inspection.

Additionally, in the above-described fifth aspect or the above-described configurations, the beam-diameter adjusting means may be configured such that it is capable of adjusting the distance between the transmitting diaphragm and the emission position of the laser light.

Furthermore, in the above-described fifth aspect or the above-described configurations, the laser device may be provided with a plurality of optical fibers having differing diameters, each emitting laser light, and the beam-diameter adjusting means may be configured such that it selects one of the optical fibers to be used.

In addition, a sixth aspect of the present invention is an ultrasonic inspection method including a laser device that emits output-adjusted laser light; an ultrasonic-wave transmitting unit having a transmitting diaphragm that generates ultrasonic waves upon being irradiated with the laser light emitted by the laser device; and beam-diameter adjusting means for adjusting the beam diameter of the laser light radiated on the transmitting diaphragm, the method including adjusting the beam diameter by the beam-diameter adjusting means; generating ultrasonic waves, whose intensity corresponds to the types of inspection subject and the type of inspection, by the transmitting diaphragm; and carrying out inspection by radiating these ultrasonic waves on a test object.

With this aspect, the transmitting diaphragm is irradiated with the output-adjusted laser light emitted by the laser device, and thus, the transmitting diaphragm generates ultrasonic waves, and because these ultrasonic waves are radiated on a test object, it is possible to prevent degradation or deformation of the test object.

Accordingly, high-power laser light can be handled, and therefore, the intensity of the generated ultrasonic waves can be increased. Thus, preferable inspection can by carried out.

At this time, the size of the beam diameter is adjusted by the beam-diameter adjusting means; the transmitting diaphragm generates ultrasonic waves having an intensity in accordance with the type of inspection object and the type of inspection; and inspection is carried out by irradiating the test object with these ultrasonic waves. Therefore, it is possible to carry out inspection of differing characteristics, for example, surface inspection wherein a surface is inspected by imaging it and volumetric inspection for inspecting internal flaws, i.e. hybrid inspection.

In addition, a seventh aspect of the present invention is an atomic power plant nondestructive inspection method wherein nondestructive inspection of an atomic power plant is carried out by using the ultrasonic inspection device described above that efficiently generates sufficiently intense ultrasonic waves by radiating the laser light on the transmitting diaphragm.

In this way, because the ultrasonic inspection device that efficiently generates sufficiently intense ultrasonic waves by radiating the laser light on the transmitting diaphragm is employed, it is possible to carry out inspection in places where the laser light cannot pass through, for example, in sodium, which is used as coolant for a fast-breeder reactor.

With the present invention, the transmitting diaphragm generates ultrasonic waves upon being irradiated with the laser light emitted by the laser device, and because these ultrasonic waves are radiated on a test object, it is possible to prevent degradation or deformation of the test object.

Accordingly, high-power laser light can be handled, and therefore, the intensity of the generated ultrasonic waves can be increased. Thus, preferable inspection can by carried out.

In addition, by providing the beam-diameter adjusting means, it is possible to cope with changes in the types of test object, inspection location, etc. with a single the ultrasonic inspection device. For example, it is possible to carry out inspection of differing characteristics, such as volumetric inspection and surface inspection, i.e. hybrid inspection.

EXPLANATION OF REFERENCE SIGNS

Figure 1:
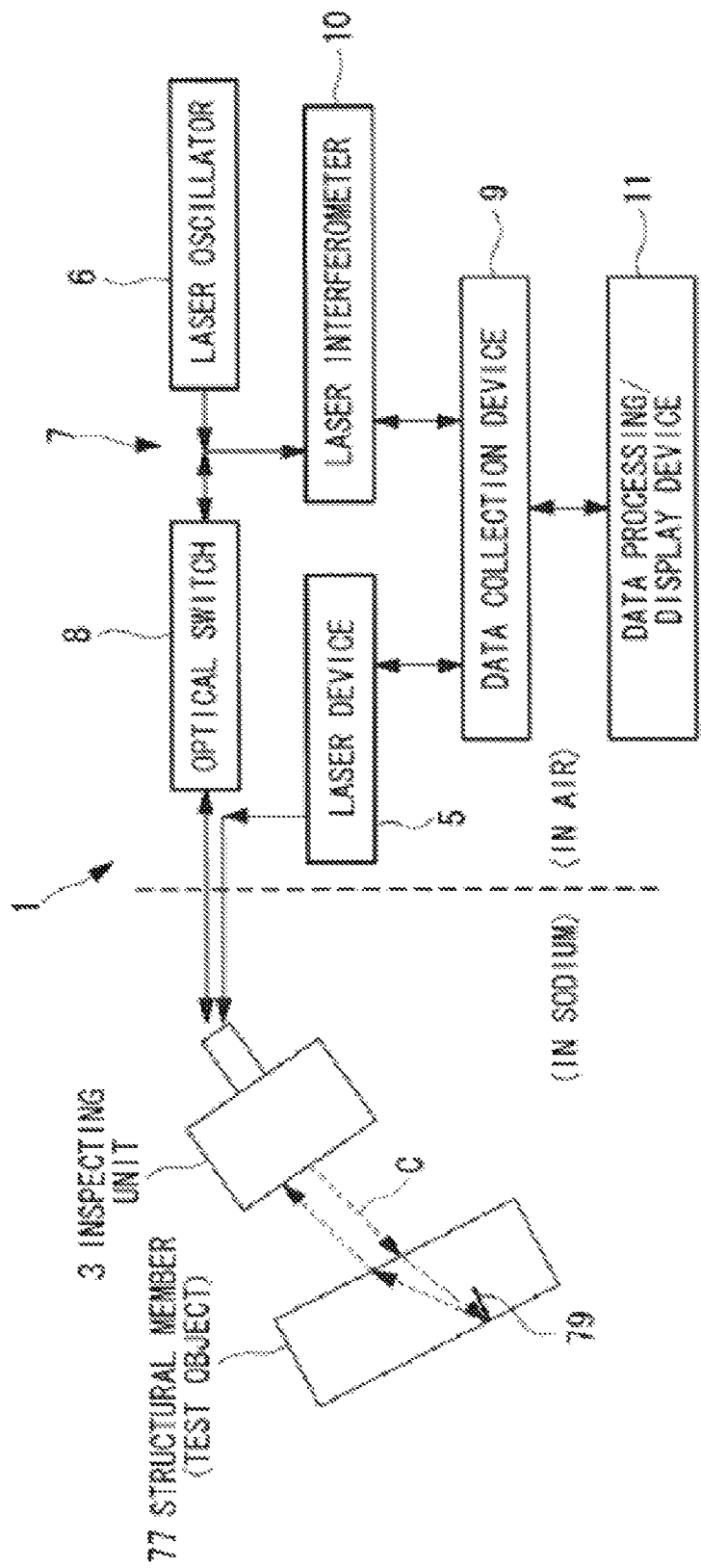
FIG. 1 is a block diagram showing, in outline, the overall configuration of an ultrasonic inspection device according to an embodiment of the present invention.

1: ultrasonic inspection device
5: laser device
17: volumetric-inspection ultrasonic-wave transmitting unit
19: surface-inspection ultrasonic-wave transmitting unit 23: optical fiber
39: transmitting diaphragm
51: optical fiber
53: receiving diaphragm
55: beam-diameter adjusting means
71: composite
75: sapphire diaphragm
77: structural member
81: viscous member

BEST MODE FOR CARRYING OUT THE INVENTION

An ultrasonic inspection device 1 according to one embodiment of the present invention will be described below, based on FIGS. 1 to 5. The ultrasonic inspection device 1 is for carrying out the ultrasonic testing of members in sodium, which is used as coolant for a fast-breeder reactor, and for carrying out volumetric inspection for inspecting the internal condition and surface inspection for inspecting the surface condition.

FIG. 1 is a block diagram showing, in outline, the overall configuration of the ultrasonic inspection device 1.

The ultrasonic inspection device 1 includes an inspecting unit 3 that transmits and receives ultrasonic waves, a laser device 5 that emits laser light for ultrasonic wave transmission, a receiving laser unit 7 that receives and emits laser light for ultrasonic wave reception, a data collection device 9 that stores transmitted and received data and instructs operations of the laser device 5 and the receiving laser unit 7, and a data processing/display device 11 that processes and displays the transmitted and received data.

The receiving laser unit 7 is provided with a laser oscillator 6 for generating laser light, an optical switch 8 for guiding the laser light into and out of optical fibers, and a laser interferometer 10 for causing interference of transmitting laser light and receiving laser light.

Figure 2:
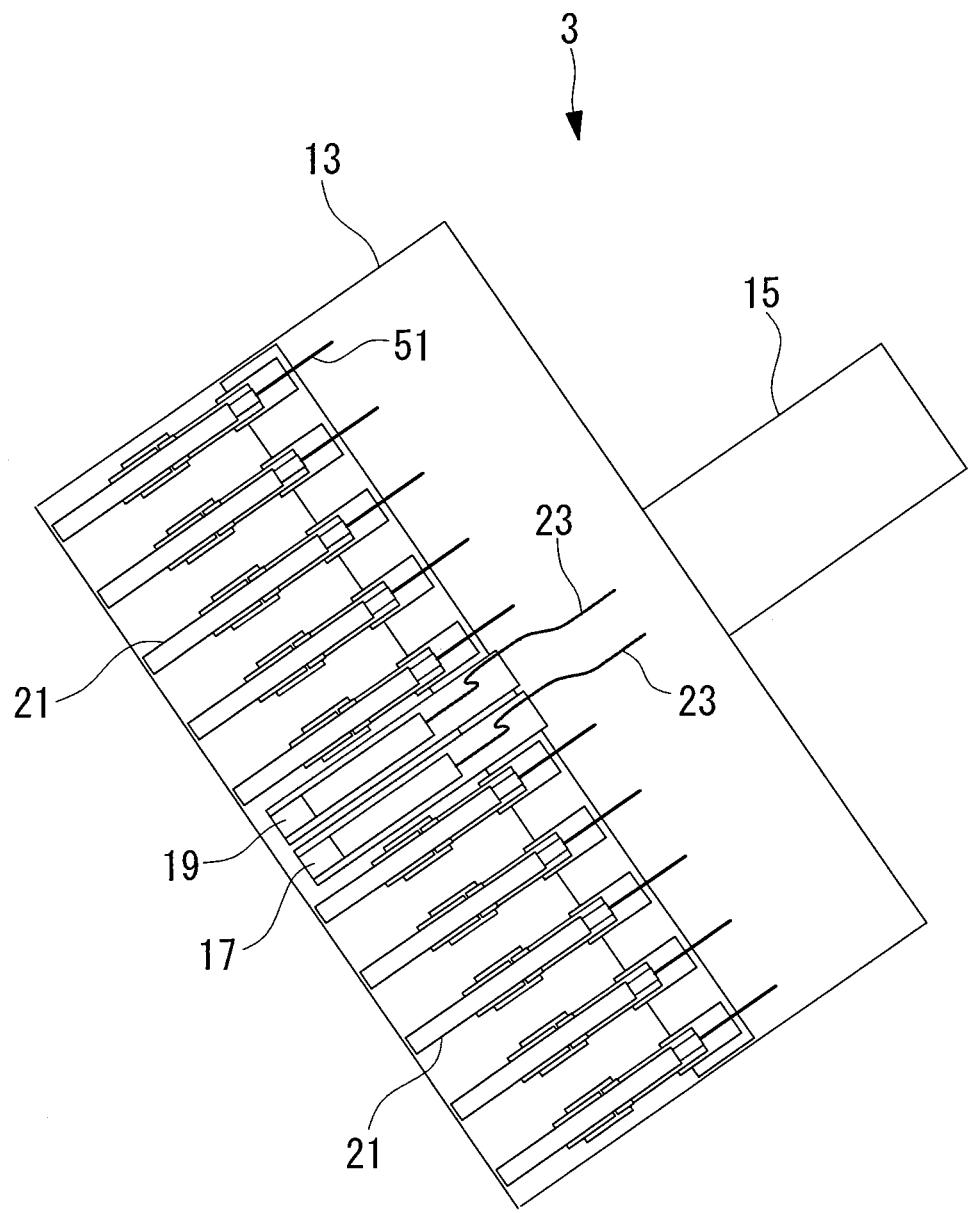
FIG. 2 is a sectional view showing, in outline, the configuration of an inspecting unit according to an embodiment of the present invention.

FIG. 2 is a sectional view showing, in outline, the configuration of the inspecting unit 3.

The inspecting unit 3 is provided with a body 13 that is a substantially rectangular box, a cylindrical channel portion 15, attached on one surface of the body in a substantially center portion thereof, through which the optical fibers are inserted, a volumetric-inspection ultrasonic-wave transmitting unit (ultrasonic-wave transmitting unit) 17 attached inside the body 13, a surface-inspection ultrasonic-wave transmitting unit (ultrasonic-wave transmitting unit) 19, and a plurality of ultrasonic-wave receiving units 21.

The volumetric-inspection ultrasonic-wave transmitting unit 17, the surface-inspection ultrasonic-wave transmitting unit 19, and the ultrasonic-wave receiving units 21 have substantially cylindrical shapes and are attached so as to have axes in a direction that intersects with the surface of the body 13 to which the channel portion 15 is attached and on a side of the body 13 away from the channel portion 15.

A plurality of the ultrasonic-wave receiving units 21 are arranged in a matrix (for example, 10 rows by 10 columns) at substantially equal intervals.

The volumetric-inspection ultrasonic-wave transmitting unit 17 and the surface-inspection ultrasonic-wave transmitting unit 19 are both installed in a substantially center portion of the ultrasonic-wave receiving units 21.

Figure 3:
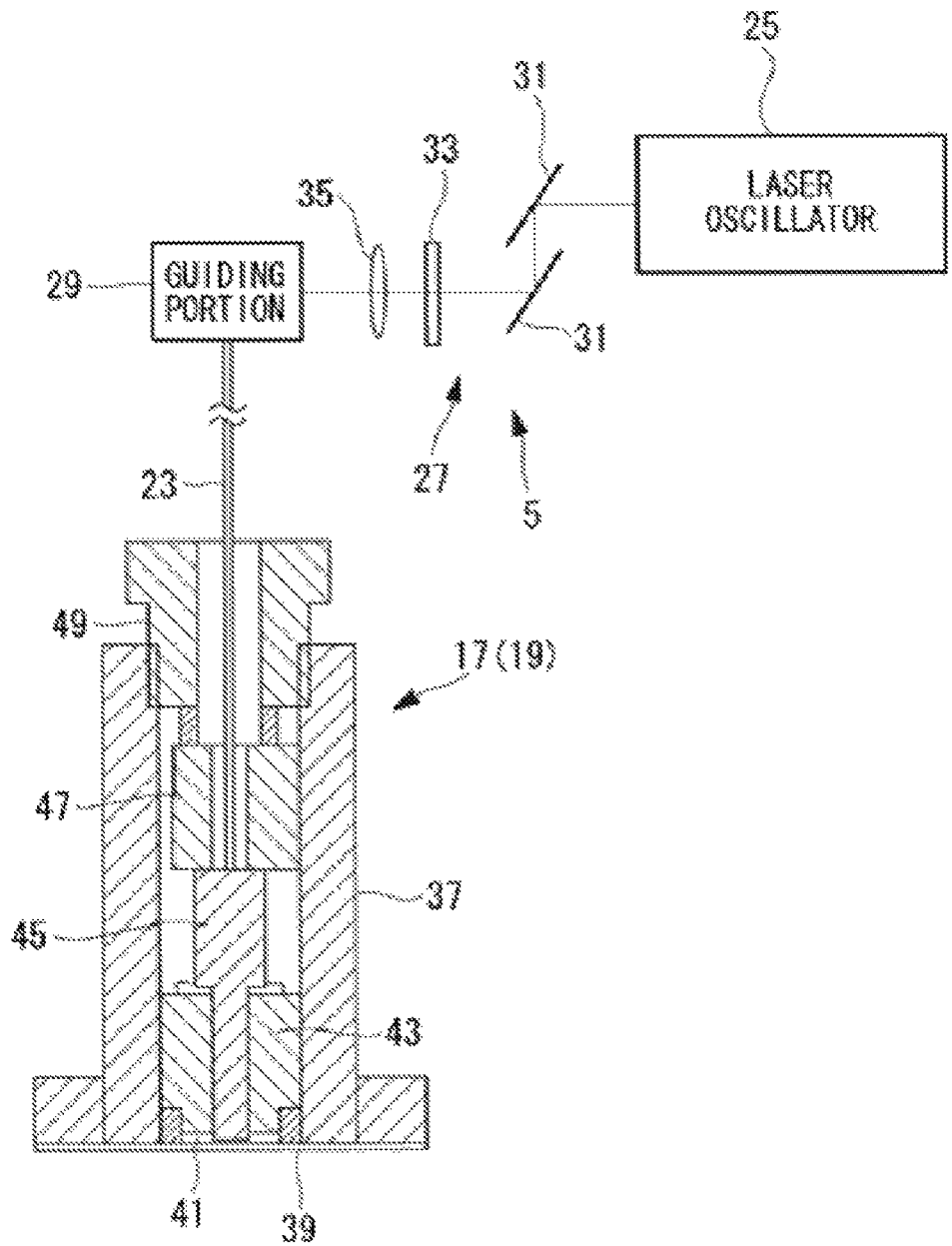
FIG. 3 is a block diagram showing, in outline, the configuration of an ultrasonic-wave transmitting system according to an embodiment of the present invention.

The volumetric-inspection ultrasonic-wave transmitting unit 17 and the surface-inspection ultrasonic-wave transmitting unit 19 are connected to the laser device 5 via respective optical fibers 23 (see FIGS. 2 and 3).

Because the structures of the volumetric-inspection ultrasonic-wave transmitting unit 17 and the surface-inspection ultrasonic-wave transmitting unit 19 are substantially the same, the volumetric-inspection ultrasonic-wave transmitting unit 17 will be described.

The laser device 5 is provided with a laser oscillator 25, a laser light path 27, and a guiding portion 29, which is constituted, for example, of an optical switch, etc., for guiding the laser light into the optical fibers 23.

The laser light path 27 is provided with a pair of mirrors 31, an ND filter 33, and a focusing lens 35.

The ND filter 33 is provided with a plurality of exchangeable filters and, by exchanging these, adjusts the intensity of the laser light, that is, the output.

The focusing lens 35 is movable along the laser light path 27 to enable adjustment, to some degree, of the diameter of laser light that enters the optical fibers 23 (the diameter of the laser light that is made incident on a transmitting diaphragm 39 described below).

The volumetric-inspection ultrasonic-wave transmitting unit 17 is provided with a hollow substantially cylindrical body 37, the transmitting diaphragm 39 attached to one end portion of the body 37, a heat resistant damper 41, a backup ring 43 that is installed on the other end portion thereof and that supports the transmitting diaphragm 39, a ferrule 45, which is a connecting member, that is disposed at the other end portion of the backup ring 43 and that arranges the optical fibers 23 in a predetermined positional relationship, a decentering ring 47 that holds down the ferrule 45 and that is disposed at the other end portion of the ferrule 45, and a holding screw 49 that holds down members disposed on one end side of the body 37 and that is screwed into a hollow portion in the other end portion thereof.

The volumetric-inspection ultrasonic-wave transmitting unit 17 and the surface-inspection ultrasonic-wave transmitting unit 19 are installed so that the transmitting diaphragm 39 faces the surface opposing the channel portion 15 of the body 13.

Figure 4:
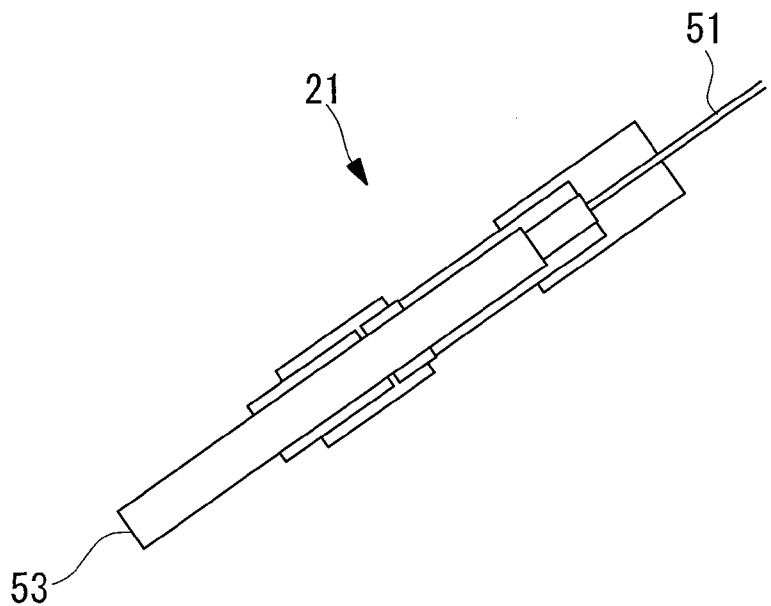
FIG. 4 is a sectional view showing, in outline, the configuration of an ultrasonic-wave receiving unit according to an embodiment of the present invention.

FIG. 4 is a sectional view showing, in outline, the configuration of the ultrasonic-wave receiving unit 21.

The ultrasonic-wave receiving unit 21 is formed in a substantially cylindrical shape and is connected at one end to an optical fiber 51, which connects to the optical switch 8. A receiving diaphragm 53 is attached to the other end portion of the ultrasonic-wave receiving unit 21.

The ultrasonic-wave receiving units 21 are installed so that the receiving diaphragms 53 face the surface opposing the channel portion 15 of the body 13.

Figure 6:
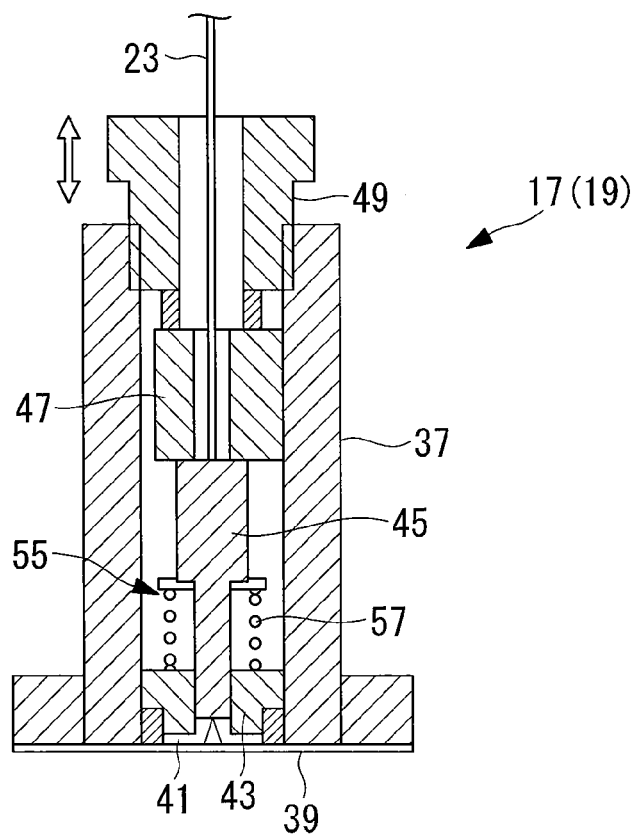
FIG. 6 is a sectional view showing another form of a volumetric-inspection ultrasonic-wave transmitting unit according to an embodiment of the present invention.
Figure 7:
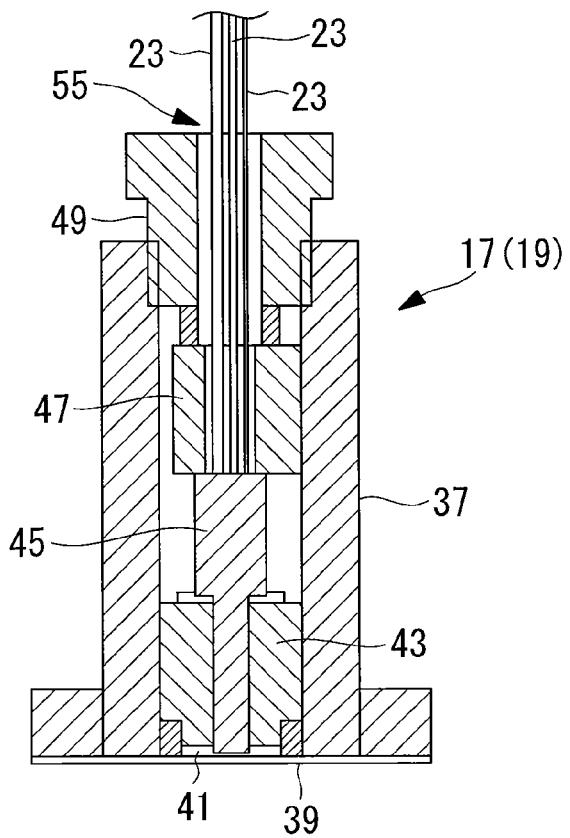
FIG. 7 is a sectional view showing another form of a volumetric-inspection ultrasonic-wave transmitting unit according to an embodiment of the present invention.
Figure 8:
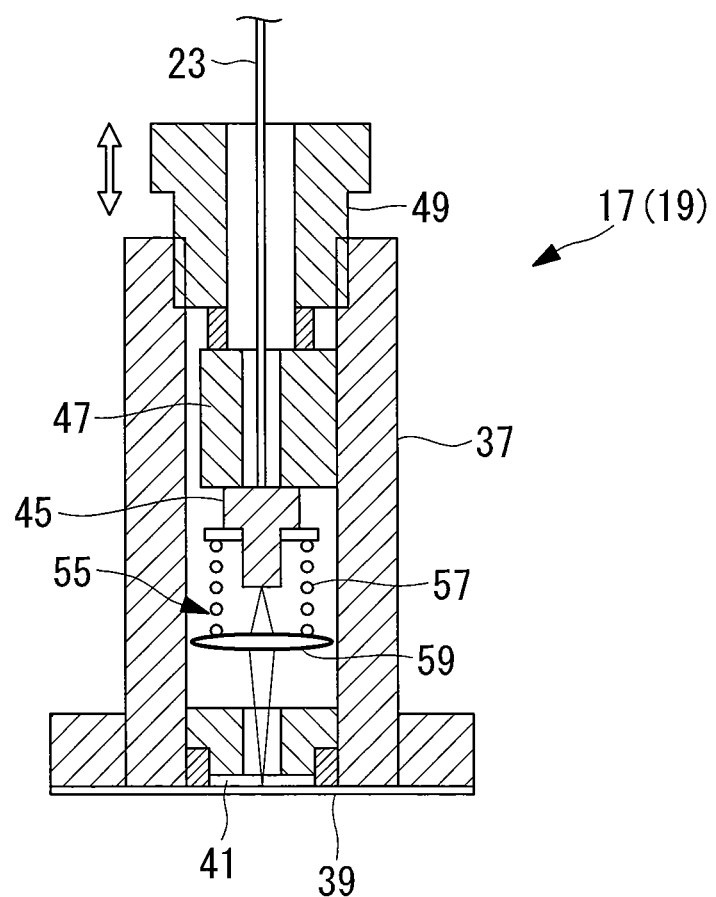
FIG. 8 is a sectional view showing another form of a volumetric-inspection ultrasonic-wave transmitting unit according to an embodiment of the present invention.

Note that the volumetric-inspection ultrasonic-wave transmitting unit 17 and the surface-inspection ultrasonic-wave transmitting unit 19 may be provided with beam-diameter adjusting means 55 such as those shown in FIGS. 6 to 8, in addition to the focusing lens 35.

The volumetric-inspection ultrasonic-wave transmitting unit 17 shown in FIG. 6 is provided with a compression spring 57 that constantly biases the ferrule 45 toward the holding screw 49. When the holding screw 49 is rotated to be moved outward in the axial direction, the ferrule 45 is pressed by the compression spring 57 and is similarly moved outward with respect to the axial direction. When the holding screw 49 is rotated in the opposite direction to be moved toward the transmitting diaphragm 39, the ferrule 45 is moved toward the transmitting diaphragm 39 against the biasing force of the compression spring 57.

Accordingly, the distance between the tip of the ferrule 45 and the transmitting diaphragm 39 changes. When this distance changes, the beam diameter of the laser light reaching the transmitting diaphragm 39 changes depending on the radiation angle of the laser light emitted from the tip of the ferrule 45.

Note that the structure for changing the distance between the emission end of the optical fiber 51 (for example, the tip of the ferrule 45) and the transmitting diaphragm 39 is not limited to the one shown in FIG. 6; and various structures are possible.

The volumetric-inspection ultrasonic-wave transmitting unit 17 shown in FIG. 7 is provided with a plurality of the optical fibers 23 having differing diameters. Because the beam diameters of the laser light emitted from the optical fibers 23 differ depending on the diameters thereof, the beam diameter of the laser light reaching the transmitting diaphragm 39 can be changed by selecting the optical fiber 23 to be used in the laser device 5.

In the volumetric-inspection ultrasonic-wave transmitting unit 17 shown in FIG. 8, a convex lens 59 is attached so as to be movable in the axial direction between the ferrule 45 and the transmitting diaphragm 39. In addition, the ferrule 45 is, similarly to the one in FIG. 6, constantly biased toward the holding screw 49 by the compression spring 57.

By moving the convex lens 59 in the axial direction, the focusing state of the laser light is changed, thereby changing the beam diameter of the laser light reaching the transmitting diaphragm 39.

Note that in FIG. 8, the beam diameter of the laser light reaching the transmitting diaphragm 39 is changed by moving the convex lens 59 in the axial direction. However, it is not limited to this; for example, the ferrule 45 may be moved in the axial direction, or both the convex lens 59 and the ferrule 45 may be moved in the axial direction.

When the laser light is radiated on the transmitting diaphragm 39, the transmitting diaphragm 39 generates ultrasonic waves.

Figure 5:
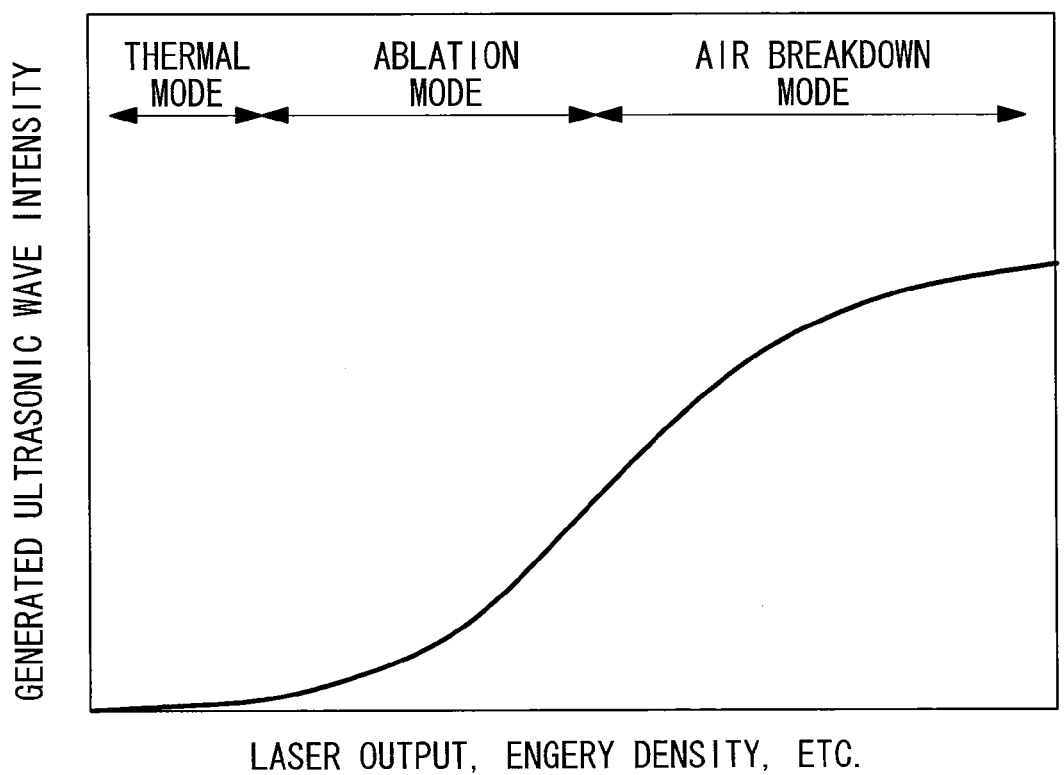
FIG. 5 is a graph showing the relationship between the laser intensity and the intensity of generated ultrasonic waves.

At this time, the intensity of the generated ultrasonic waves correspondingly changes with the laser light output or the energy density of the laser light, as shown by the solid line in FIG. 5.

In a range where the laser light output or the energy density of the laser light, etc., is low (low energy range), the energy of the laser light is used up in increasing the temperature of the transmitting diaphragm 39, etc., and thus, the intensity of the generated ultrasonic waves is low. This portion is referred to as the thermal mode.

When the laser light output or the energy density of the laser light, etc., increases further, the intensity of the generated ultrasonic waves abruptly increases. Because the transmitting diaphragm 39 is currently being ablated by the laser light in this step, it is referred to as the ablation mode.

When the laser light output or the energy density of the laser light, etc., increases even further, the ablation of the transmitting diaphragm 39 increases, causing vaporization of a portion thereof, and the laser light is scattered or absorbed; therefore, the proportion of the energy supplied to the transmitting diaphragm 39 by the laser light decreases.

Once this occurs, because the rate of increase of the intensity of the generated ultrasonic waves diminishes, the energy efficiency of the laser light decreases. This state is referred to as the air breakdown mode.

Therefore, considering the energy efficiency and damage to the transmitting diaphragm 39, the intensity of the laser light (the laser light output or the energy density of the laser light, etc.) is selected within the ablation mode range.

The material, dimensions, etc. of the transmitting diaphragm 39 are selected by taking into consideration the intensity of the laser light from the laser device 5, and the intensity and the frequency characteristics of ultrasonic waves generated thereby. In order to improve the energy efficiency, it is preferable that the transmitting diaphragm 39 be of material with a high laser light absorption efficiency.

In this way, because the material properties and characteristics of the transmitting diaphragm 39 have considerable influence on the performance of the ultrasonic inspection device 1, evaluation tests were carried out regarding these.

Figure 9:
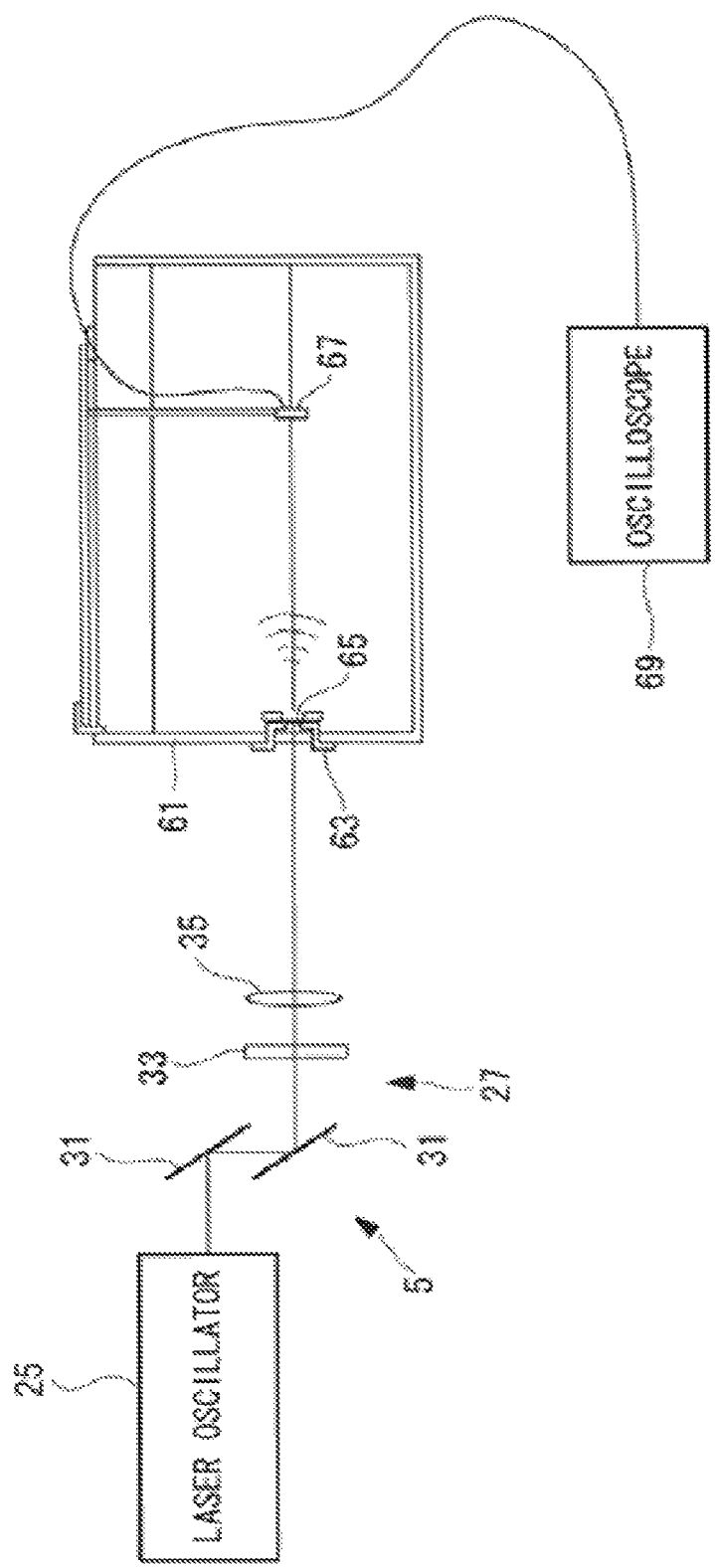
FIG. 9 is a block diagram showing, in outline, the configuration of a test device.

FIG. 9 shows a testing device for carrying out these evaluation tests.

Surelite I-10 manufactured by Continuum, Inc. used as the laser oscillator 25 emits YAG laser light. The YAG laser light the laser oscillator 25 outputs was set to have an output of 400 mJ, a pulse interval of 10 Hz, and a pulse width of 10 ns.

A diaphragm specimen 65 is attached to a mounting member 63 provided on one surface of a tank 61 holding water, the ultrasonic waves generated by radiating the laser light from the laser oscillator 25 on this diaphragm specimen 65 are received by a receiving piezoelectric element 67, and the intensity thereof is measured by an oscilloscope 69.

Stainless steel (SUS), titanium (Ti), aluminum (Al), copper (Cu), and tin (Sn) were used as the diaphragm specimen 65. The diaphragm specimen 65 is a circular plate having a diameter of 25 mm and a thickness of 0.05 mm. In the case of SUS, one with a thickness of 0.03 mm was used in order to examine the effect of the thickness.

Figure 10:
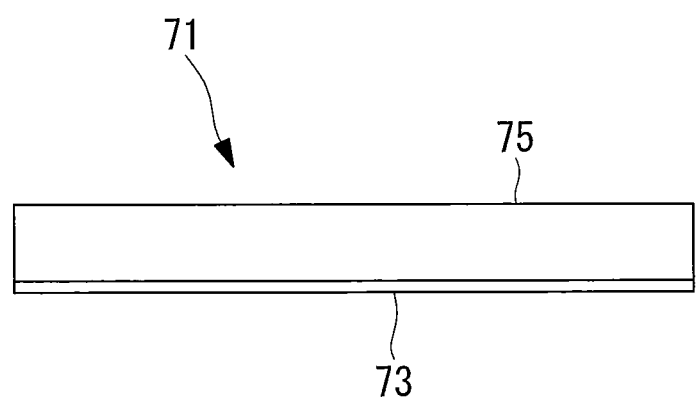
FIG. 10 is a sectional view showing, in outline, the configuration of a composite.

In addition, a composite 71 shown in FIG. 10 was also tested as the diaphragm specimen 65. The composite 71 is a SUS diaphragm (transmitting diaphragm) 73, having a thickness of 0.03 mm, one surface of which, that is, the surface on the side on which the laser light is made incident, is bonded to a sapphire diaphragm (optical member) 75 of sapphire glass having a thickness of 1 mm. The composite 71 is a circular plate having a diameter of 30 mm.

With the composite 71, the bonding surface of the SUS diaphragm 73 is sputtered with Cr—Ni—Au. On the other hand, the bonding surface of the sapphire diaphragm 75 is metalized. Then, the composite 71 is formed by bonding together the bonding surfaces of the SUS diaphragm 73 and the sapphire diaphragm 75 with Au—Su solder. The solder layer is substantially 2 μm.

Figure 11:
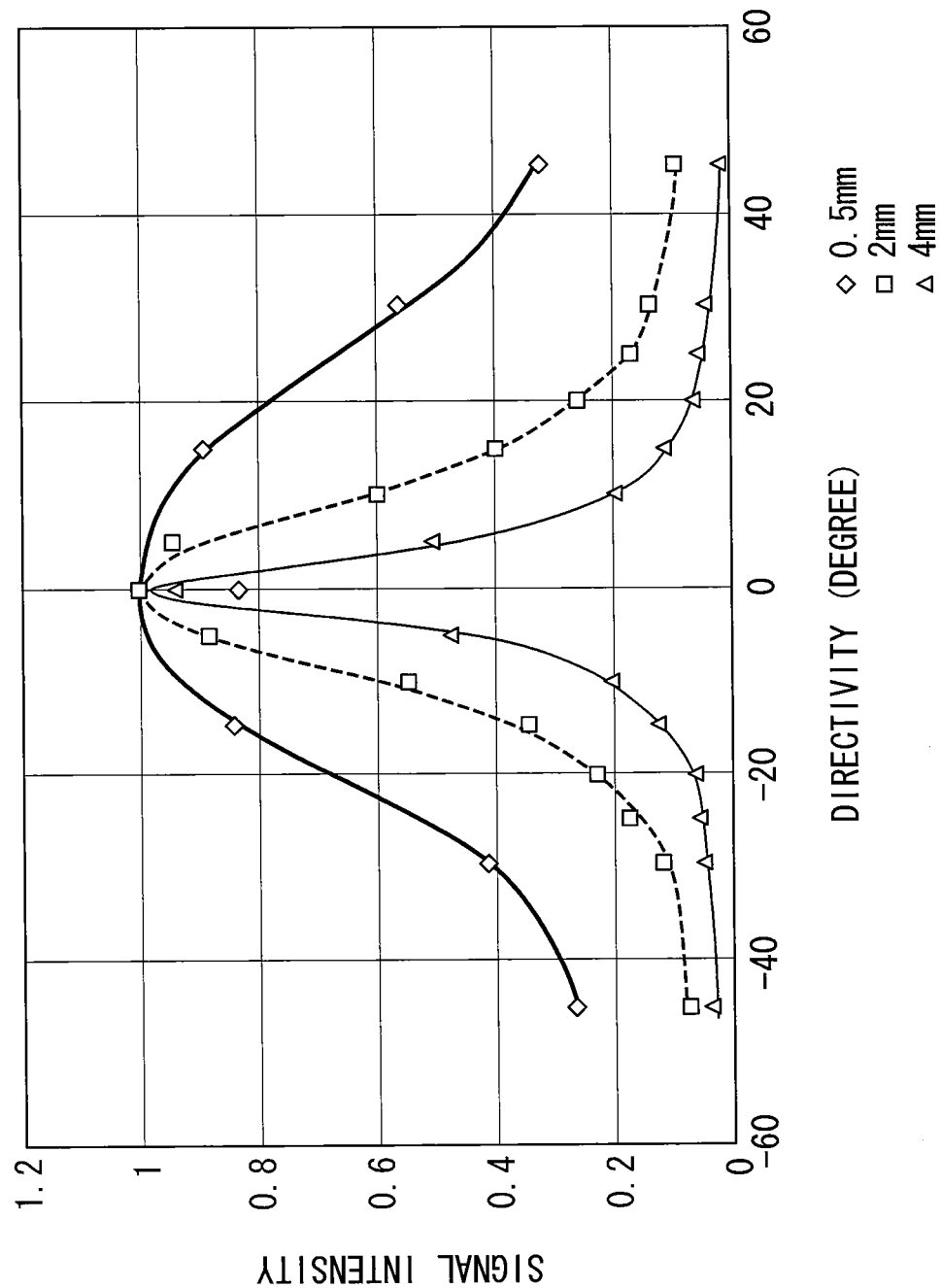
FIG. 11 is a graph showing differences in the directivity, with beam diameter as a parameter.

FIG. 11 shows the directivity with the beam diameter of the laser light as a parameter. Note that, in order to make the state of the directivity easily understood, the signal intensity (ultrasonic wave intensity) is normalized.

Viewing this, the directivity is high with the beam diameter of 0.5 mm (high-intensity ultrasonic waves can be output in a wide region), the directivity is low with the beam diameter of 4 mm (high-intensity ultrasonic waves are output concentrated in a limited region), and the directivity is intermediate with the beam diameter of 2 mm.

In other words, it was found that the directivity increases with decreasing beam diameter.

It is speculated that this is because the ablation ratio per unit area increases with decreasing beam diameter.

Figure 12:
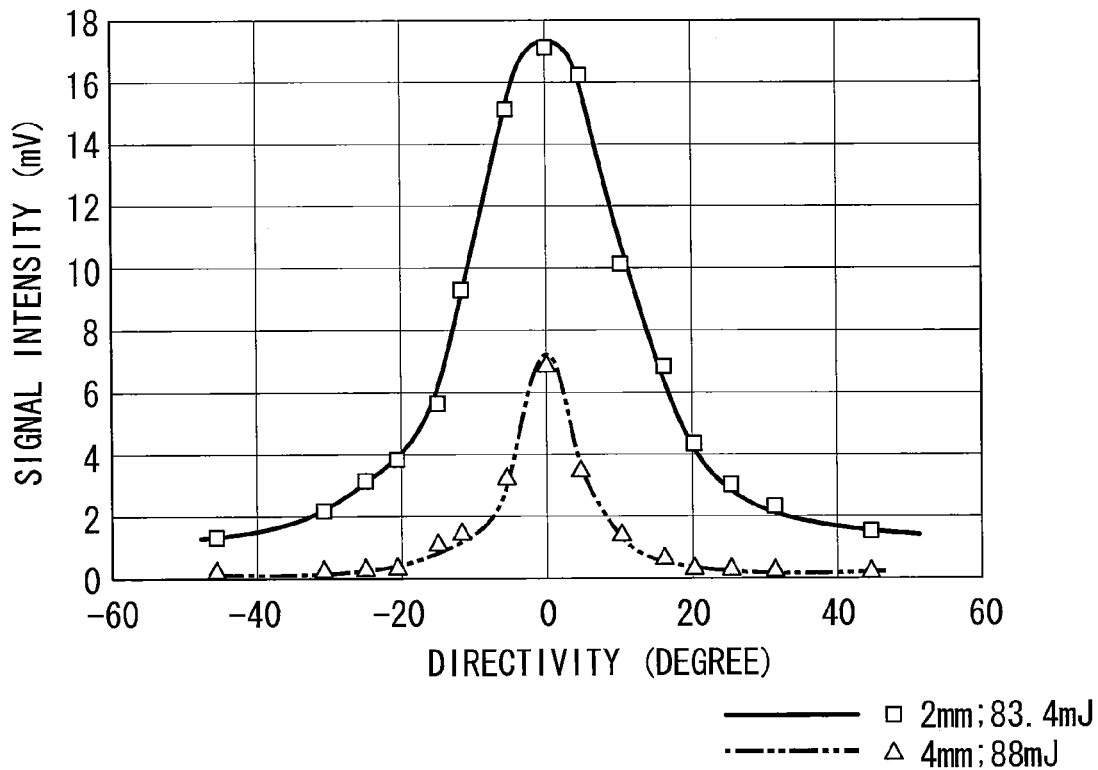
FIG. 12 is a graph showing differences in the signal intensity by beam diameter under a constant input energy condition.
Figure 13:
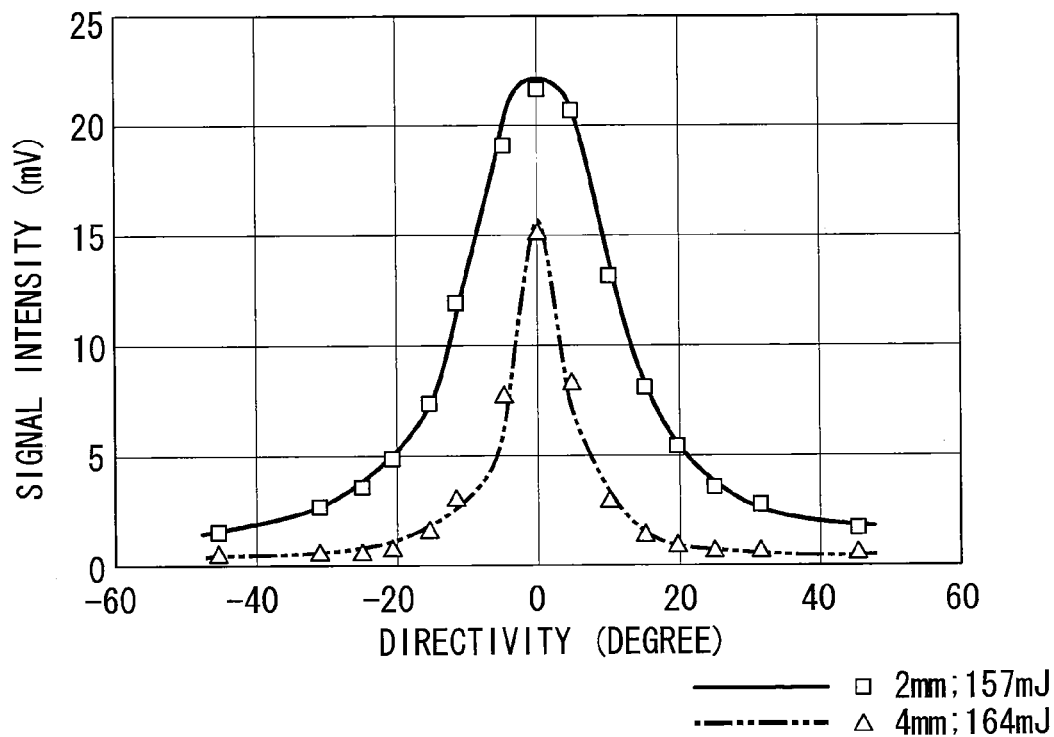
FIG. 13 is a graph showing differences in the signal intensity by beam diameter under a constant input energy condition.

FIGS. 12 and 13 show the relationship between the signal intensity and the directivity with the beam diameter of the laser light as a parameter, where the input energy is kept constant in the low energy range (thermal mode).

Viewing this, the total signal intensity is greater for the beam diameter of 2 mm than it is for the beam diameter of 4 mm, by factors of approximately 4 in FIG. 12 and approximately 2.4 in FIG. 13.

In other words, if the input energy is constant, as the beam diameter decreases, the intensity of the generated ultrasonic waves increases, that is, the energy conversion efficiency increases.

Figure 14:
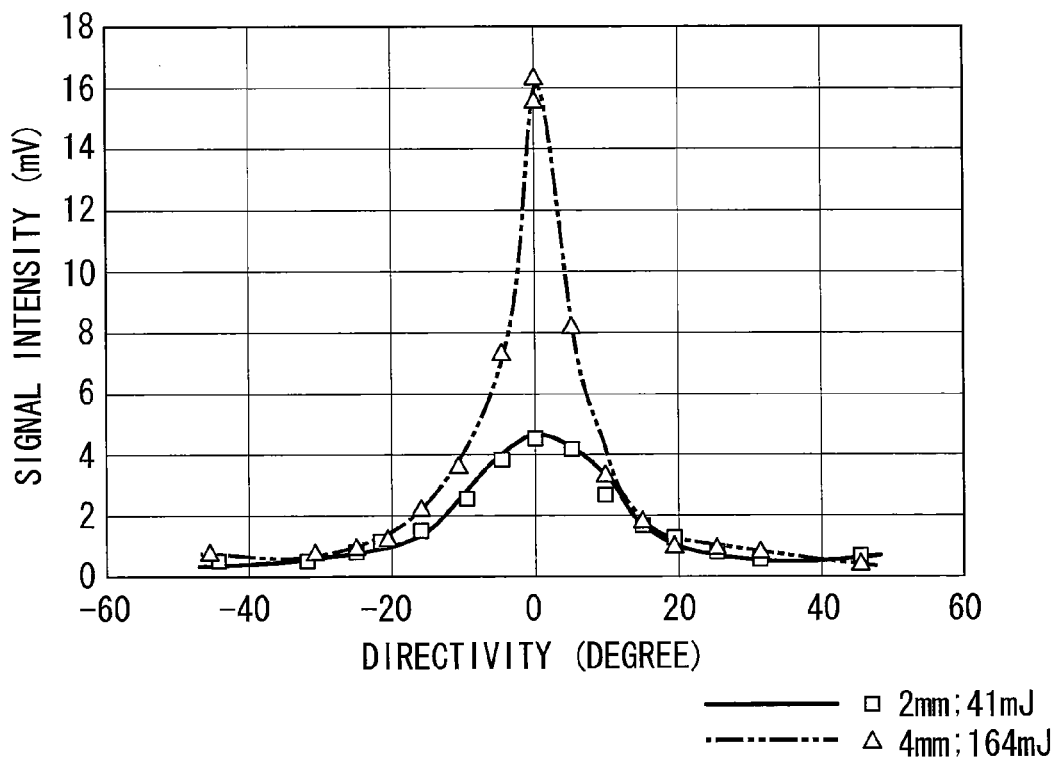
FIG. 14 is a graph showing differences in the signal intensity by beam diameter under a constant input energy per unit area condition.
Figure 15:
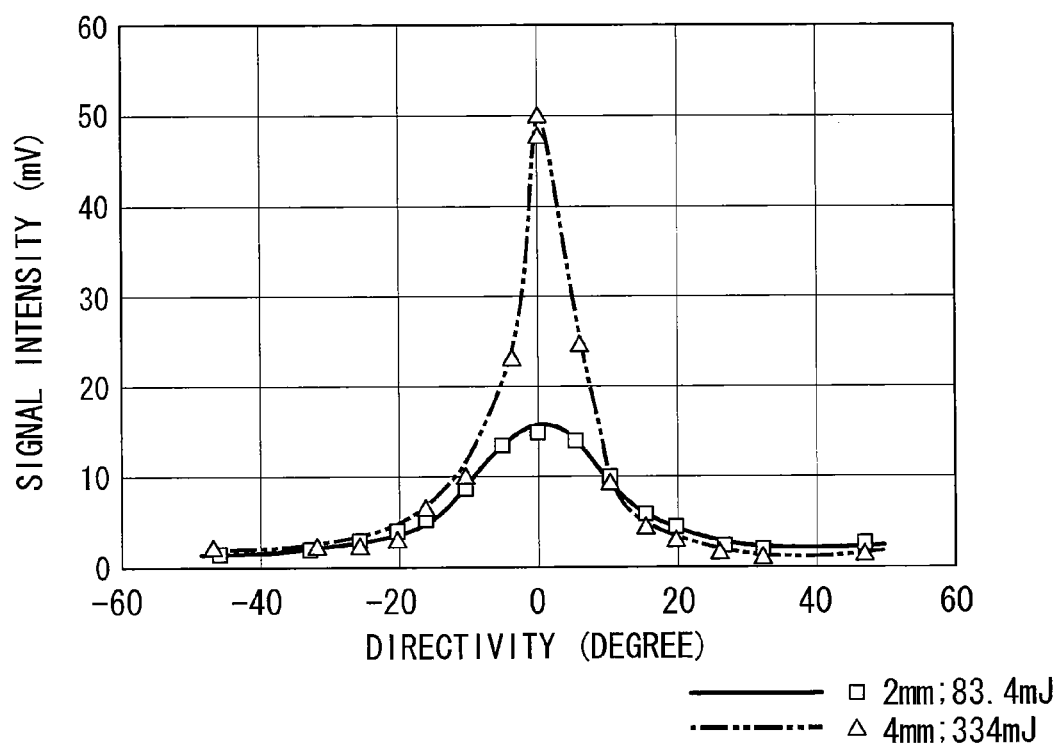
FIG. 15 is a graph showing differences in the signal intensity by beam diameter under a constant input energy per unit area condition.

FIGS. 14 and 15 show the relationship between the signal intensity and the directivity with the beam diameter of the laser light as a parameter, where the input energy per unit area is made the same.

Viewing this, the total signal intensity is greater for the beam diameter of 4 mm than it is for the beam diameter of 2 mm, by factors of approximately 1.32 in FIG. 14 and approximately 1.14 in FIG. 15.

In other words, if the input energy per unit area is constant, as the beam diameter increases, the intensity of the generated ultrasonic waves increases, that is, the energy conversion efficiency increases.

In this way, it was found that the beam diameter of the laser light considerably influences the energy efficiency.

Figure 16:
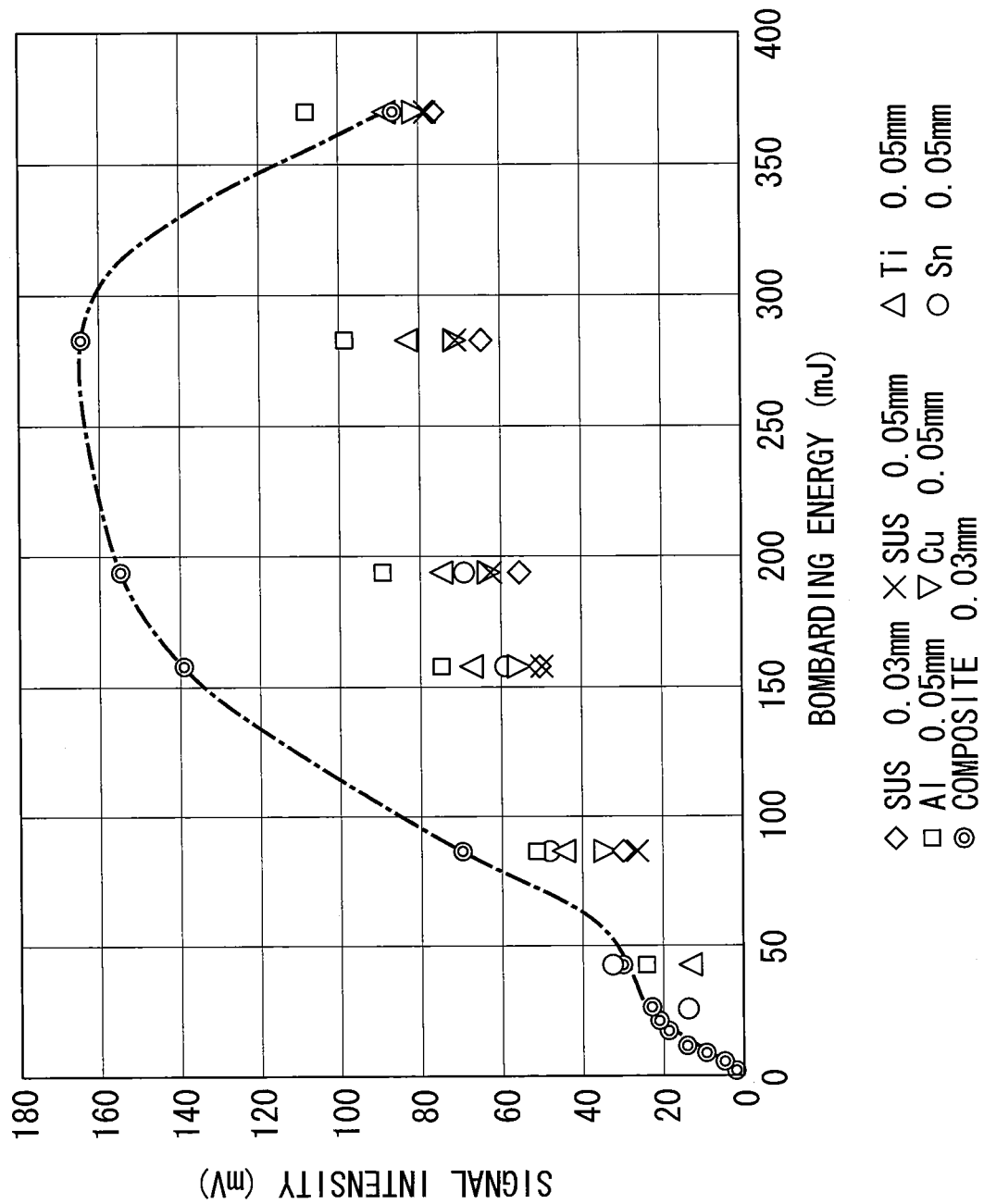
FIG. 16 is a graph showing the intensity of ultrasonic wave generation by different types of materials in the ablation mode range.
Figure 17:
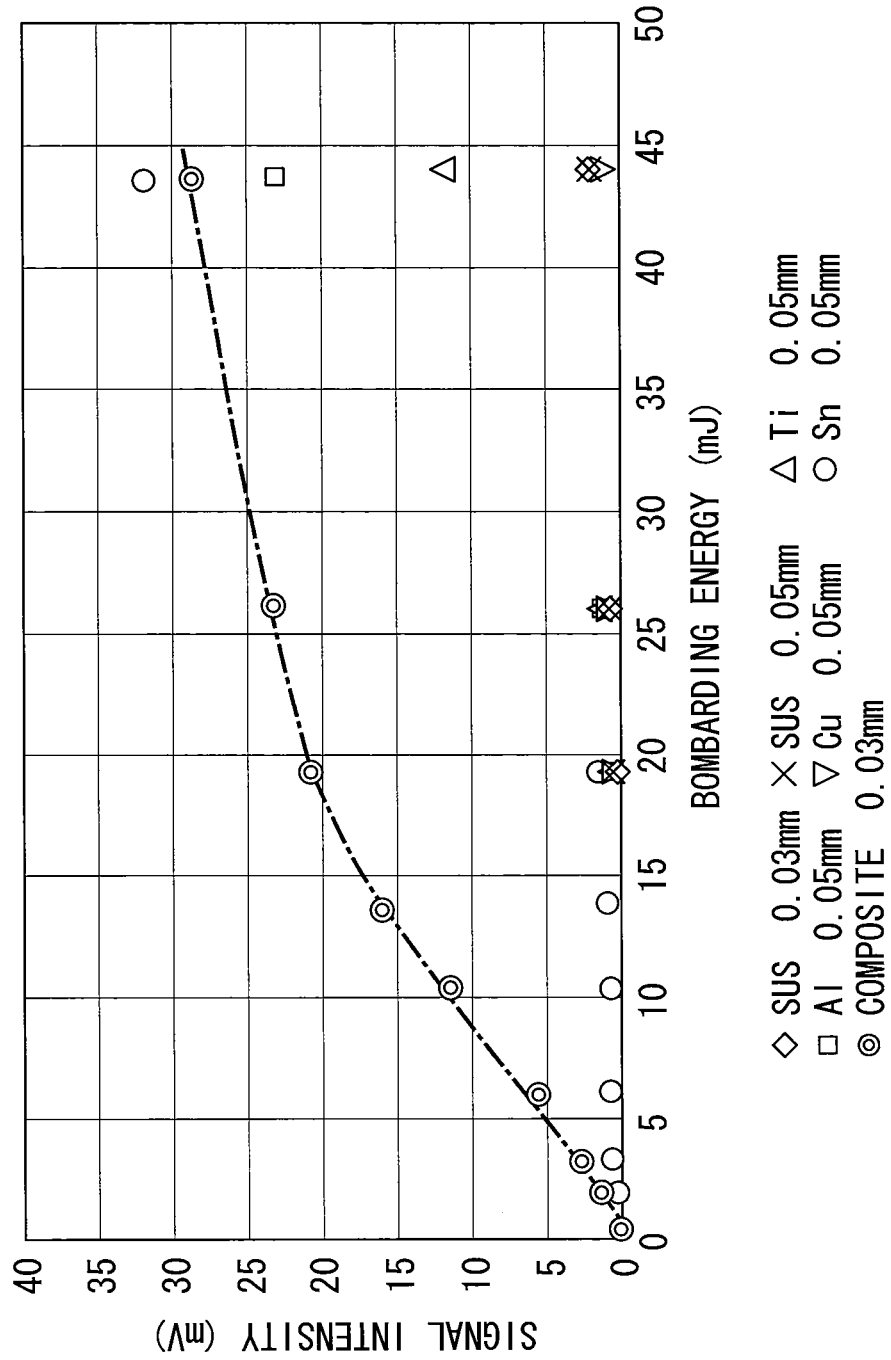
FIG. 17 is a graph showing the intensity of ultrasonic wave generation by different types of materials in the low ablation mode range.
Figure 18:
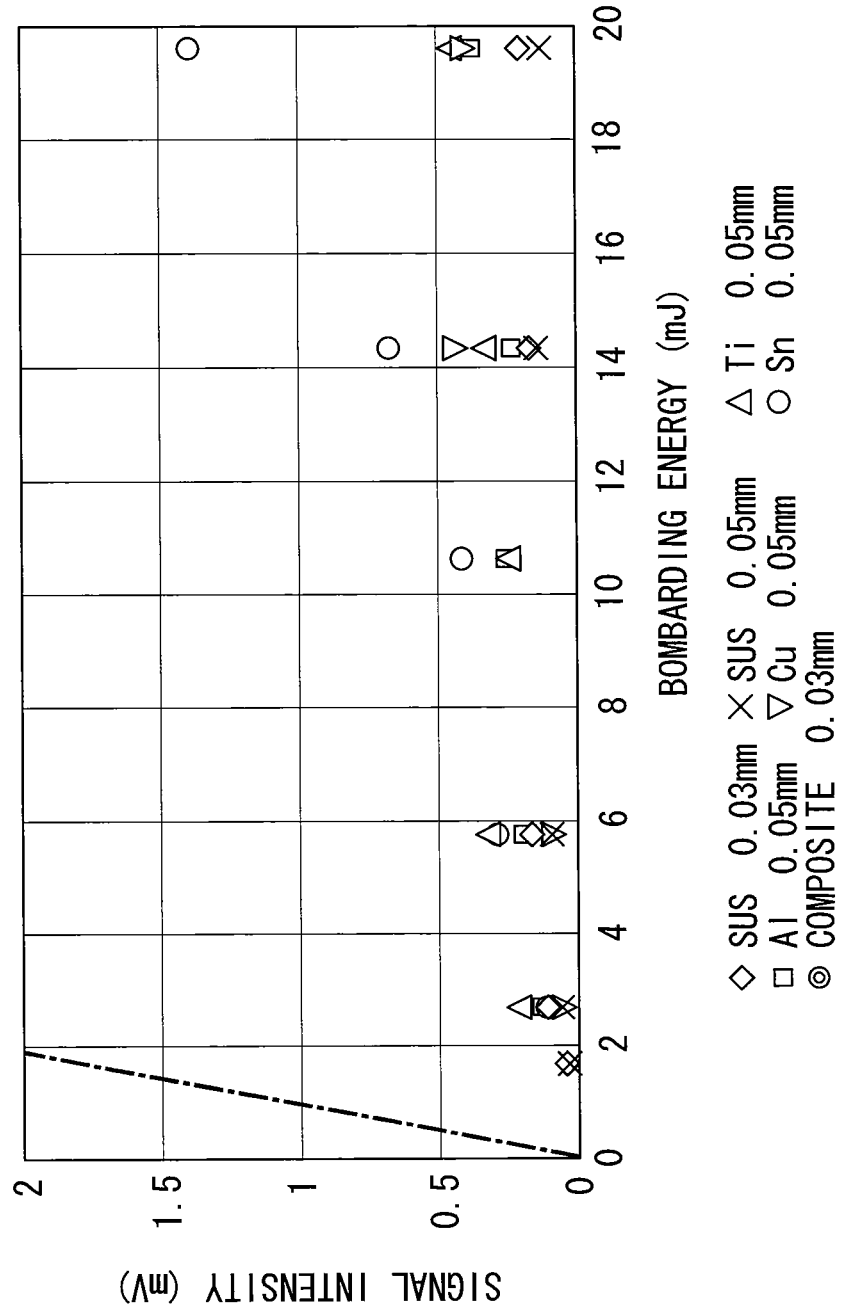
FIG. 18 is a graph showing the intensity of ultrasonic wave generation by different types of materials in the thermal mode range.

In FIGS. 16 to 18, the intensity of the ultrasonic waves is compared by types of material. FIG. 16 mainly shows a state in the ablation mode range (substantially 80 mJ or greater). FIG. 17 shows a state in the low ablation mode range (approximately 50 mJ). FIG. 18 shows a state in the thermal mode range (25 mJ or lower).

In each figure, a trend in the measurement results for the composite 71 is indicated by a one-dot chain line.

In the ablation mode range (FIG. 16), aluminum shows the highest ultrasonic wave intensity (high energy conversion efficiency), followed by titanium, then SUS. In addition, with respect to SUS, with which the diaphragm specimens 65 of differing thickness were tested, no significant differences in ultrasonic wave intensity due to thickness were detected.

With tin, a hole was bored through in the center of the diaphragm specimen 65 during the test. Because tin is soft, it was found not to be suitable for practical use.

It was found that SUS and copper are also capable of producing sufficiently practical ultrasonic wave intensity.

The ultrasonic wave intensity obtained for the composite 71 was about 1.6 times greater than that for aluminum and more than about 2 times greater than that for SUS, which is the same material as the composite 71, demonstrating high energy conversion efficiency.

The sapphire glass surface melted at 300 mJ or greater, damaging the composite 71, and the ultrasonic wave intensity abruptly decreased. The upper limit for the use of the composite 71 employing sapphire glass is in this vicinity.

In the low ablation mode range (FIG. 17), tin shows the highest ultrasonic wave intensity, followed by aluminum, then titanium.

The ultrasonic wave intensity of the composite 71 is substantially equivalent to those of tin and aluminum. However, as opposed to SUS, which is the same material as the composite 71, the obtained ultrasonic wave intensity was about 10 times greater or more.

In the thermal mode range (FIG. 18), tin and titanium are relatively preferable. The ultrasonic wave intensity of the composite 71, is about 10 times greater than that of a single material (see FIG. 17).

Aluminum and titanium, whose energy efficiencies were preferable in the ablation mode range where the ultrasonic wave intensity required in practice can be obtained, were shown to be effective as material for the transmitting diaphragm 39.

In addition, the composite 71 was shown to be even more effective.

Because the laser incident side of the SUS diaphragm 73 is restrained by the sapphire diaphragm 75, when the SUS diaphragm 73 is irradiated with the laser light and deforms, the deformation thereof acts on the sapphire diaphragm 75. Then, the reaction force from the sapphire diaphragm 75 is exerted on the SUS diaphragm 73 in the direction of the ultrasonic wave generation; therefore, the intensity of the ultrasonic waves that the SUS diaphragm 73 generates is increased.

In addition, because the sapphire diaphragm 75 suppresses degradation of or damage to the SUS diaphragm 73 by the laser light, it is possible to increase the intensity of the generated ultrasonic waves by increasing the intensity of the laser light.

In the composite 71, the SUS diaphragm 73 and the sapphire diaphragm 75 are bonded together with solder; however, the bonding method is not limited to solder, and suitable means can be employed, or they may be arranged so as to be adjacent to each other without bonding. It is sufficient so long as the sapphire diaphragm 75 is installed so as to restrain the SUS diaphragm 73.

The material for the optical member constituting the composite 71 is not limited to sapphire glass; ceramic such as oxidized aluminum film, etc., silica glass, or the like may be employed.

Instead of the SUS diaphragm 73, a diaphragm of aluminum, titanium, copper, tin or the like may be employed.

The transmitting diaphragm 39 may have the surface coated with, for example, an oxidized film of iron or aluminum. These oxidized films can improve the laser light absorptivity, and can suppress degradation of and damage to the transmitting diaphragm 39.

Figure 19:
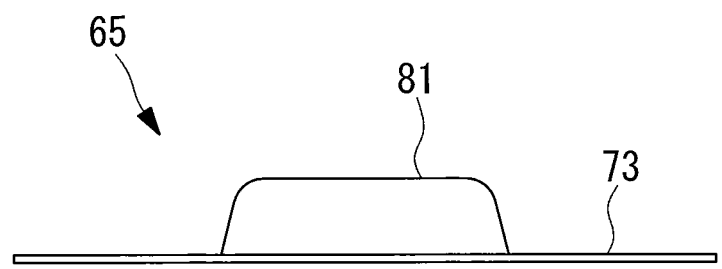
FIG. 19 is sectional view showing, in outline, the configuration of a diaphragm sample having a viscous member attached thereto.

Tests were carried out using one having the structure shown in FIG. 19 as the diaphragm specimen 65. The diaphragm specimen 65 is, for example, a SUS diaphragm with a thickness of 0.02 mm and having a viscous member (viscous material) 81 applied on one surface, that is, the surface on the laser incident side. The SUS diaphragm 73 is a circular plate having a diameter of 30 mm.

As the viscous member 81, for example, "Pyrogel GR 100" (product name), made by SONOTECH Inc. of the United States, is employed. This is a contact medium employed as a couplant. This viscous member 81 includes glycerin as the main ingredient, is transparent and jelly-like, and has a wide operating temperature range of from −45.6° C. to 427° C. (−50° F. to 800° F.). In addition, the viscosity is high at $4 \times 10^6$ cps or higher, and once attached, it is not easily washed off.

The viscous member 81 is applied by hand to thickness of substantially 1 mm over a region including and exceeding the region on which the laser light is radiated.

Under the condition where the laser input energy is 10 mJ and the beam diameter of the incident laser light is 2 mm, changes over time in the magnitude of the generated ultrasonic waves were examined using a diaphragm specimen 65 with the viscous member 81 and a diaphragm specimen 65 (a SUS diaphragm 73 having a thickness of 0.02 mm) without the viscous member 81.

Figure 20:
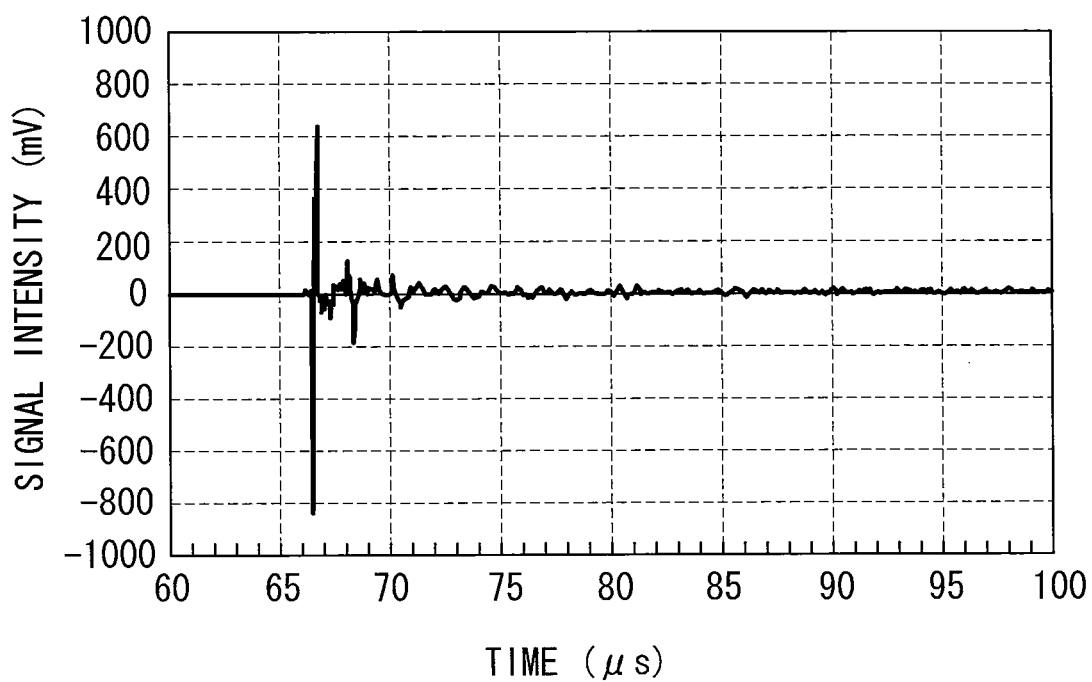
FIG. 20 is a graph showing the intensity of ultrasonic wave generation by the diaphragm sample having a viscous member attached thereto.
Figure 21:
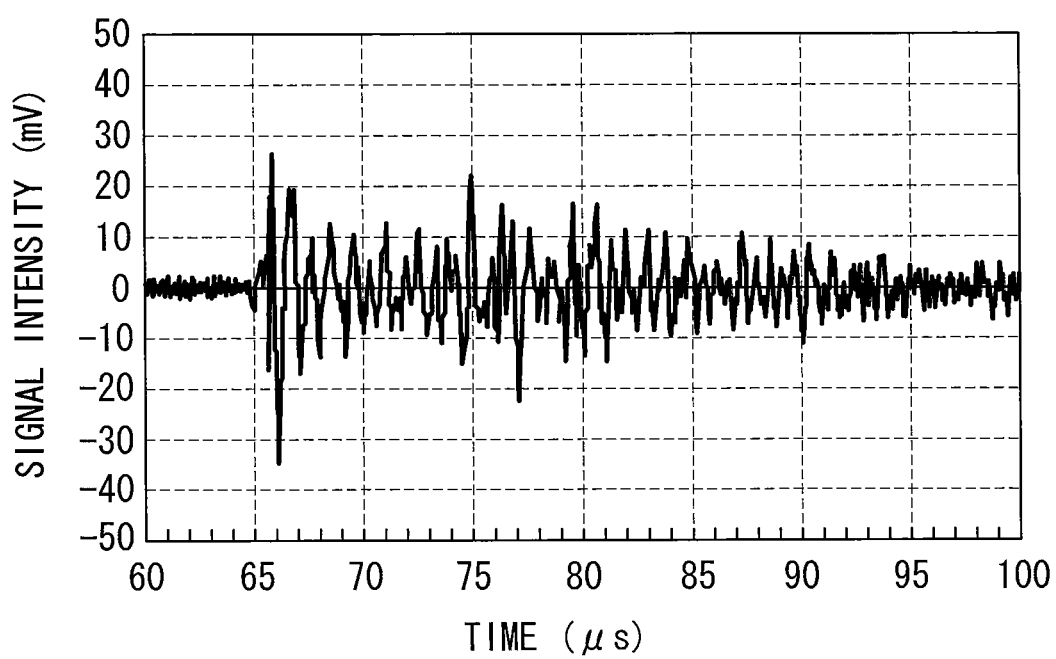
FIG. 21 is a graph showing the intensity of ultrasonic wave generation by a diaphragm sample without a viscous member.

FIG. 20 is the result for the diaphragm specimen 65 with the viscous member 81. FIG. 21 is the result for the SUS diaphragm 73 alone.

Viewing this, with the diaphragm specimen 65 with the viscous member 81, as compared with the SUS diaphragm 73 alone, the intensity of the generated ultrasonic waves was greater by a factor of about 20 and a sharp ultrasonic waveform was obtained.

Of vibrations generated at the SUS diaphragm 73 by radiating the laser light on the SUS diaphragm 73, vibrations directed toward the laser incident side are reflected backwards by the viscous member 81; therefore, these vibrations are directed in the direction of the ultrasonic wave generation. In this way, because the vibrations directed in the direction of the ultrasonic wave generation are superimposed on the vibrations directed in the opposite direction and reflected backward, the intensity of the ultrasonic waves generated by the SUS diaphragm 73 is increased.

Because the viscous member 81 is easily deformed, it can be made to adhere to the surface of the SUS diaphragm 73 without a gap. Accordingly, because the viscous member 81 can reflect back the vibrations of the SUS diaphragm 73 over the entire surface thereof, energy can be efficiently transmitted in the direction of the ultrasonic wave generation.

Because the transparent viscous member 81 does not prevent the passage of the laser light, more laser light is made incident on the SUS diaphragm 73, thereby making it possible to increase the intensity of the generated ultrasonic waves.

The region over which the viscous member 81 is applied need not be the entire surface, so long as at least the region that is irradiated with the laser light is covered. It is more desirable that the viscous member 81 be applied so as to cover portions where the ultrasonic wave generation is greater, beyond the region that is irradiated with the laser light.

Here, test results are described for the transmitting diaphragm 39 made of SUS; however, the intensity of generated ultrasonic waves can similarly be increased by ones constituted of aluminum, titanium, copper, tin, or the like.

The operation of the ultrasonic inspection device 1 according to the above-described embodiment will be described.

The inspecting unit 3 is disposed facing an inspection subject, the structural member (test object) 77. When carrying out volumetric inspection for inspecting a flaw 79 inside the structural member 77, the volumetric-inspection ultrasonic-wave transmitting unit 17 is used.

When the laser oscillator 25 generates laser light, the laser light enters the guiding portion 29 via the laser light path 27. The laser light is converted in the guiding portion 29 to a form that can pass through the optical fiber 23 at the volumetric-inspection ultrasonic-wave transmitting unit 17. This converted laser light passes through the optical fiber 23 and is radiated on the transmitting diaphragm 39 from the ferrule 45.

When the transmitting diaphragm 39 is irradiated with the laser light, the transmitting diaphragm 39 generates ultrasonic waves.

In this way, ultrasonic waves C, generated by the transmitting diaphragm 39 of the volumetric-inspection ultrasonic-wave transmitting unit 17 are radiated toward the structural member 77.

These ultrasonic waves C are adjusted such that the frequency is mainly 2 to 5 MHz. In other words, conditions, including the material and dimensions of the transmitting diaphragm 39, the laser light intensity of the laser device 5, etc., are set such that the frequency of the generated ultrasonic waves C becomes mainly 2 to 5 MHz.

The ultrasonic waves C radiated on the structural member 77 are reflected at the structural member 77 and directed toward the inspecting unit 3, thus vibrating the receiving diaphragms 53 of individual ultrasonic-wave receiving units 21. If the structural member 77 has a flaw 79, the ultrasonic waves C are redirected by the flaw 79, thereby shifting the phase of the vibrations of the diaphragms 53 at this time relative to the predetermined state.

Laser light is generated by the laser oscillator 6 of the receiving laser unit 7 and is radiated on the receiving diaphragms 53 via the optical switch 8 and the optical fibers 51. The radiated laser light is reflected at the receiving diaphragms 53 and is returned to the laser interferometer 10 via the reverse route.

Because the receiving diaphragms 53 are vibrating, the distance traveled by the laser light leaving the laser oscillator and returning to the laser interferometer 10 fluctuates. By making the returning laser light interfere with the transmitting laser light from the laser oscillator 6, the fluctuation becomes noticeable.

These data are stored in the data collection device 9, and the data processing/display device 11 processes the stored data, determines the presence or absence of a flaw 79 and the location thereof when there is a flaw 79, and displays the result.

Next, when carrying out surface inspection for inspecting the surface condition of the structural member 77, the surface-inspection ultrasonic-wave transmitting unit 19 is used.

In this case, ultrasonic waves C generated by the transmitting diaphragm 39 of the surface-inspection ultrasonic-wave transmitting unit 19 are adjusted such that the frequency is mainly 10 MHz. In other words, conditions, including the material and dimensions of the transmitting diaphragm 39, the laser light intensity of the laser device 5, etc., are set such that the frequency of the generated ultrasonic waves C becomes mainly 10 MHz.

When the frequency of the ultrasonic waves C is set to be mainly 10 MHz in this way, the ultrasonic waves C are reflected at the surface without entering deep inside the structural member 77; therefore, the surface condition can be inspected.

Because the inspection operation is similar to that of the volumetric inspection, the redundant description will be omitted herein.

In this way, because the ultrasonic inspection device 1 is provided with the volumetric-inspection ultrasonic-wave transmitting unit 17 and the surface-inspection ultrasonic-wave transmitting unit 19, having different frequencies of the generated ultrasonic waves C, by employing them in a switching fashion, inspection of differing characteristics, such as volumetric inspection and surface inspection, that is, hybrid inspection, can be carried out with a single unit.

Accordingly, inspection precision, inspection efficiency, etc. can be improved by employing the ultrasonic inspection device 1 provided with optimal transmitting diaphragms 39 in accordance with the types of the structural member 77 and the type of inspection.

In this way, the transmitting diaphragm 39 generates the ultrasonic waves C upon being irradiated with the laser light emitted by the laser device 5, and because these ultrasonic waves C are radiated on the structural member 77, degradation and deformation of the structural member 77 can be prevented.

Because this allows the handling of high-power laser light, the intensity of the generated ultrasonic waves C can be increased. Accordingly, preferable inspection can be carried out.

In addition, because satisfactory inspection can be carried out even if the distance to the structural member 77 is large, the beam spread angle can be made large. This allows the resolution to be reduced, and therefore, inspection precision can be improved.

Furthermore, by using optical fibers 23 and 51 for transmitting the laser light, the volumetric-inspection ultrasonic-wave transmitting unit 17 and the surface-inspection ultrasonic-wave transmitting unit 19 can be made small; therefore, the ultrasonic inspection device 1 can be reduced in size.

Additionally, because the ultrasonic waves C are used for inspection, it is possible to carry out inspection even in places through which laser light cannot pass, for example, in sodium, which is used as coolant for a fast-breeder reactor.

In addition, as shown in FIGS. 6 to 8, with the ones provided with the beam-diameter adjusting means 55 for adjusting the beam diameter of the laser light, the beam diameter of the laser light that is made incident on the transmitting diaphragm 39 is adjusted.

For example, when the beam diameter is reduced, increasing the directivity, it is possible to carry out surface inspection for inspecting a surface by imaging it. On the other hand, when the beam diameter is increased, decreasing the directivity, volumetric inspection for inspecting internal flaws can be carried out.

In this way, by providing the beam-diameter adjusting means 55, the volumetric-inspection ultrasonic-wave transmitting unit 17 bears the function of the volumetric-inspection ultrasonic-wave transmitting unit 17 itself as well as that of the surface-inspection ultrasonic-wave transmitting unit 19; thus, for example, the surface-inspection ultrasonic-wave transmitting unit 19 can be omitted. In other words, it is possible to carry out inspection of differing characteristics such as volumetric inspection and surface inspection, that is, hybrid inspection, with the volumetric-inspection ultrasonic-wave transmitting unit 17 alone.

For example, the directivity can be altered by deforming the transmitting diaphragm 39, forming irregularities in the surface thereof.

Note that the present invention is not limited to this embodiment, and various modifications can be made without departing from the spirit of the present invention.

For example, it is not required to simultaneously include the volumetric-inspection ultrasonic-wave transmitting unit 17 and the surface-inspection ultrasonic-wave transmitting unit 19, and one or the other can be provided depending on the purpose.

The invention claimed is:

1. An ultrasonic inspection device comprising:
   a laser device that emits output-adjusted laser light;
   an ultrasonic-wave transmitting unit having a transmitting diaphragm that generates ultrasonic waves upon being irradiated with the laser light emitted by the laser device; and
   a plurality of ultrasonic-wave receiving units which are arranged in a matrix,
   wherein the ultrasonic inspection device is adapted to carry out inspection by irradiating a test object with the ultrasonic waves generated by the transmitting diaphragm of the ultrasonic-wave transmitting unit,
   wherein the ultrasonic-wave transmitting unit comprises a volumetric-inspection ultrasonic-wave transmitting unit and a surface-inspection ultrasonic-wave transmitting unit which are both installed in a substantially center portion of the ultrasonic-wave receiving units, and
   wherein the transmitting diaphragm is formed of titanium.

2. The ultrasonic inspection device according to claim 1, comprising:
   a beam-diameter adjuster for adjusting the beam diameter of the laser light radiated on the transmitting diaphragm.

3. The ultrasonic inspection device according to claim 2, wherein the beam-diameter adjuster is configured so as to adjust the distance between the transmitting diaphragm and the emission position of the laser light.

4. The ultrasonic inspection device according to claim 3, wherein the laser device is provided with a plurality of optical fibers having differing diameters and respectively transmitting the laser light, and
   wherein the beam-diameter adjuster selects one of the optical fibers to be used.

5. An atomic power plant nondestructive inspection method wherein nondestructive inspection of an atomic power plant is carried out by using an ultrasonic inspection device according to claim 1.

6. An ultrasonic inspection device comprising:
   a laser device that emits output-adjusted laser light;
   an ultrasonic-wave transmitting unit having a transmitting diaphragm that generates ultrasonic waves upon being irradiated with the laser light emitted by the laser device; and
   a plurality of ultrasonic-wave receiving units which are arranged in a matrix,
   wherein the ultrasonic inspection device is adapted to carry out inspection by irradiating a test object with the ultrasonic waves generated by the transmitting diaphragm of the ultrasonic-wave transmitting unit,
   wherein the ultrasonic-wave transmitting unit comprises a volumetric-inspection ultrasonic-wave transmitting unit and a surface-inspection ultrasonic-wave transmitting unit which are both installed in a substantially center portion of the ultrasonic-wave receiving units, and
   wherein the transmitting diaphragm is formed of aluminum.

7. The ultrasonic inspection device according to claim 6, comprising:
   a beam-diameter adjuster for adjusting the beam diameter of the laser light radiated on the transmitting diaphragm.

8. The ultrasonic inspection device according to claim 7, wherein the beam-diameter adjuster is configured so as to adjust the distance between the transmitting diaphragm and the emission position of the laser light.

9. The ultrasonic inspection device according to claim 7, wherein the laser device is provided with a plurality of optical fibers having differing diameters and respectively transmitting the laser light,
   wherein the beam-diameter adjuster selects one of the optical fibers to be used.

10. An atomic power plant nondestructive inspection method wherein nondestructive inspection of an atomic power plant is carried out by using an ultrasonic inspection device according to claim 6.

11. An ultrasonic inspection device comprising:
    a laser device that emits output-adjusted laser light;
    an ultrasonic-wave transmitting unit having a transmitting diaphragm that generates ultrasonic waves upon being irradiated with the laser light emitted by the laser device; and
    a plurality of ultrasonic-wave receiving units which are arranged in a matrix,
    wherein the ultrasonic inspection device is adapted to carry out inspection by irradiating a test object with the ultrasonic waves generated by the transmitting diaphragm of the ultrasonic-wave transmitting unit,
    wherein the ultrasonic-wave transmitting unit comprises a volumetric-inspection ultrasonic-wave transmitting unit and a surface-inspection ultrasonic-wave transmitting unit which are both installed in a substantially center portion of the ultrasonic-wave receiving units, and
    wherein the transmitting diaphragm is restrained on the laser incident side by an optical member.

12. The ultrasonic inspection device according to claim 11, comprising:
    a beam-diameter adjuster for adjusting the beam diameter of the laser light radiated on the transmitting diaphragm.

13. The ultrasonic inspection device according to claim 12, wherein the beam-diameter adjuster is configured so as to adjust the distance between the transmitting diaphragm and the emission position of the laser light.

14. The ultrasonic inspection device according to claim 12, wherein the laser device is provided with a plurality of optical fibers having differing diameters and respectively transmitting the laser light,
wherein the beam-diameter adjuster selects one of the optical fibers to be used.

15. An atomic power plant nondestructive inspection method wherein nondestructive inspection of an atomic power plant is carried out by using an ultrasonic inspection device according to claim 11.

16. An ultrasonic inspection device comprising:
a laser device that emits output-adjusted laser light;
an ultrasonic-wave transmitting unit having a transmitting diaphragm that generates ultrasonic waves upon being irradiated with the laser light emitted by the laser device; and
a plurality of ultrasonic-wave receiving units which are arranged in a matrix,
wherein the ultrasonic inspection device carries out inspection by irradiating a test object with the ultrasonic waves generated by the transmitting diaphragm of the ultrasonic-wave transmitting unit,
wherein the ultrasonic-wave transmitting unit comprises a volumetric-inspection ultrasonic-wave transmitting unit and a surface-inspection ultrasonic-wave transmitting unit which are both installed in a substantially center portion of the ultrasonic-wave receiving units, and
wherein jelly-like viscous material is applied on the laser incident side surface of the transmitting diaphragm.

17. The ultrasonic inspection device according to claim 16, comprising:
a beam-diameter adjuster for adjusting the beam diameter of the laser light radiated on the transmitting diaphragm.

18. The ultrasonic inspection device according to claim 17, wherein the beam-diameter adjuster is configured so as to adjust the distance between the transmitting diaphragm and the emission position of the laser light.

19. The ultrasonic inspection device according to claim 17, wherein the laser device is provided with a plurality of optical fibers having differing diameters and respectively transmitting the laser light,
wherein the beam-diameter adjuster selects one of the optical fibers to be used.

20. An atomic power plant nondestructive inspection method wherein nondestructive inspection of an atomic power plant is carried out by using an ultrasonic inspection device according to claim 16.

21. An ultrasonic inspection device comprising:
a laser device that emits output-adjusted laser light;
an ultrasonic-wave transmitting unit having a transmitting diaphragm that generates ultrasonic waves upon being irradiated with the laser light emitted by the laser device; and
a plurality of ultrasonic-wave receiving units which are arranged in a matrix,
wherein the ultrasonic inspection device carries out inspection by irradiating a test object with the ultrasonic waves generated by the transmitting diaphragm of the ultrasonic-wave transmitting unit,
wherein the ultrasonic-wave transmitting unit comprises a volumetric-inspection ultrasonic-wave transmitting unit and a surface-inspection ultrasonic-wave transmitting unit which are both installed in a substantially center portion of the ultrasonic-wave receiving units, and
wherein the ultrasonic inspection device further comprises a beam-diameter adjuster for adjusting the beam diameter of the laser light radiated on the transmitting diaphragm.

22. The ultrasonic inspection device according to claim 21, wherein the beam-diameter adjuster is configured so as to adjust the distance between the transmitting diaphragm and the emission position of the laser light.

23. The ultrasonic inspection device according to claim 21, wherein the laser device is provided with a plurality of optical fibers having differing diameters and respectively transmitting the laser light,
wherein the beam-diameter adjuster selects one of the optical fibers to be used.

24. An atomic power plant nondestructive inspection method wherein nondestructive inspection of an atomic power plant is carried out by using an ultrasonic inspection device according to claim 21.

25. An ultrasonic inspection method using an ultrasonic inspection device comprising:
a laser device that emits output-adjusted laser light;
an ultrasonic-wave transmitting unit having a transmitting diaphragm that generates ultrasonic waves upon being irradiated with the laser light emitted by the laser device
a plurality of ultrasonic-wave receiving units which are arranged in a matrix; and
a beam-diameter adjuster for adjusting the beam diameter of the laser light radiated on the transmitting diaphragm,
wherein the ultrasonic-wave transmitting unit comprises a volumetric-inspection ultrasonic-wave transmitting unit and a surface-inspection ultrasonic-wave transmitting unit which are both installed in a substantially center portion of the ultrasonic-wave receiving units,
the ultrasonic inspection method comprising:
adjusting the beam diameter with the beam-diameter adjuster;
generating ultrasonic waves, whose intensity corresponds to the types of inspection subject and the type of inspection, with the transmitting diaphragm; and
carrying out inspection by radiating these ultrasonic waves on a test object.

* * * * *